US008882484B2

United States Patent
Jin et al.

(10) Patent No.: US 8,882,484 B2
(45) Date of Patent: Nov. 11, 2014

(54) METHODS AND COMPOSITIONS FOR PRODUCTION OF RECOMBINANT PROTEIN IN HBX-EXPRESSING MAMMALIAN CELLS

(75) Inventors: Fang Jin, San Ramon, CA (US); Richard N. Harkins, Alameda, CA (US); Maxine Bauzon, Hercules, CA (US); Terry Hermiston, Corte Madera, CA (US)

(73) Assignee: Bayer HealthCare LLC, Whippany, NJ (US)

( * ) Notice: Subject to any disclaimer, the term of this patent is extended or adjusted under 35 U.S.C. 154(b) by 904 days.

(21) Appl. No.: 12/995,177

(22) PCT Filed: May 27, 2009

(86) PCT No.: PCT/US2009/045352
§ 371 (c)(1),
(2), (4) Date: Jul. 21, 2011

(87) PCT Pub. No.: WO2009/155008
PCT Pub. Date: Dec. 23, 2009

(65) Prior Publication Data
US 2011/0275121 A1    Nov. 10, 2011

Related U.S. Application Data

(60) Provisional application No. 61/056,634, filed on May 28, 2008.

(51) Int. Cl.
| | | |
|---|---|---|
| C12P 1/00 | (2006.01) | |
| C12P 21/06 | (2006.01) | |
| C12P 21/04 | (2006.01) | |
| C12P 21/02 | (2006.01) | |

(52) U.S. Cl.
CPC ........................ *C12P 21/02* (2013.01)
USPC .............. 425/41; 435/69.1; 435/71.1

(58) Field of Classification Search
None
See application file for complete search history.

(56) References Cited

U.S. PATENT DOCUMENTS

2006/0053502 A1   3/2006   Gao et al.
2009/0111142 A1*  4/2009   Nielsen et al. ............... 435/69.1

FOREIGN PATENT DOCUMENTS

WO    2006/028889 A2   3/2006

OTHER PUBLICATIONS

International Search Report and Written Opinion of International Application No. PCT/US09/045352 mailed Sep. 16, 2009.
International Preliminary Report on Patentability of International Application No. PCT/US09/045352 mailed Nov. 30, 2010.
Li et al., Hepatitis B virus X protein (HBx) activates ATF6 and IRE1-XBP1 pathways of unfolded protein response. Virus Research, vol. 124, pp. 44-49 (2007).
Becker et al., An XBP-1 dependent bottle-neck in production of IgG subtype antibodies in chemically defined serum-free Chinese hamster ovary (CHO) fed-batch processes. Journal of Biotechnology, Epub, vol. 135, pp. 217-223 (2008).
Jin et al., "Enhanced Protein Production Using HBV X Protein (HBx), and Synergy When Used in Combination with XBP1s in BHK21 Cells", Biotechnology and Bioengineering, vol. 105, No. 2, pp. 341-349 (2009).
Misra et al., The conserved amino-terminal region (amino acids 1-20) of the hepatitis B virus X protein shows a transrepression function, Virus Research, 105:157-165 (2004).
Schifferli et al., Transfection of Suspension Cultures of CHO Cells, Focus, 21(1):16-17 (1999).

* cited by examiner

*Primary Examiner* — Jennifer Dunston
*Assistant Examiner* — Addison D Ault
(74) *Attorney, Agent, or Firm* — Nevrivy Patent Law Group P.L.L.C.

(57) ABSTRACT

The method of the invention provides for producing a heterologous protein in mammalian host cells having nucleic acid encoding Hepatitis B X protein and the heterologous protein, by growing mammalian host cells selected from the group consisting of HKB11, CHO, BHK21, C2C12, and HEK293 cells, by growing mammalian host cells in non-adherent suspension culture, or by growing mammalian host cells which contain nucleic acid providing exogenous X-box Binding Protein, XBP1s. The conditions should be such that HBx, exogenous XBP1s if present, and the heterologous protein are expressed by the mammalian cells. The invention includes compositions for carrying out the method.

13 Claims, 10 Drawing Sheets

A

B

US 8,882,484 B2

METHODS AND COMPOSITIONS FOR PRODUCTION OF RECOMBINANT PROTEIN IN HBX-EXPRESSING MAMMALIAN CELLS

REFERENCE TO RELATED APPLICATIONS

This application claims priority to U.S. Provisional Application No. 61/056,634, which was filed May 28, 2008.

SEQUENCE LISTING

This application includes both a paper copy and electronic copy of a sequence listing. Applicants certify that the subject matter contained in the electronic copy of the sequence listing is the same as that presented in paper copy.

FIELD OF THE INVENTION

The invention relates generally to compositions and methods for production of a heterologous protein by recombinant mammalian host cells which express hepatitis B virus X protein (HBx).

BACKGROUND OF THE INVENTION

The need for recombinant proteins, including therapeutic proteins, is acute and there is a continuing need to improve the efficiency of production of recombinant proteins. Increasing protein yield during commercial production remains a significant challenge.

It has been reported that transient transfection with HBx plasmid can result in up-regulation of the expression of heterologous lymphotoxin alpha by Huh7 and Chang hepatoma cells. Lee et al., Biochim Biophys Acta 1741, 75-84 (2005). In addition, Chang hepatoma cells that are stably transfected with HBx can have up-regulated expression of lymphotoxin alpha.

It has also been reported that, in mammalian hepatocarcinoma suspension cells, transfection with HBx can reduce the level of E-cadherin expression in a dose-dependent manner. Lee et al., Oncogene 24, 6617-6625 (2005).

Secreted and membrane proteins typically undergo folding and other post-translational modifications in the endoplasmic reticulum (ER)-Golgi system of the host cells. The function of the unfolded protein response (UPR) signaling pathway is to sense unfolded protein levels and to adjust the protein folding and secretion capacity of the cells to environmental changes such as ER stress. Bernales et al., Annu. Rev. Cell Develop. Biology 22, 487-506 (2006). ER stress is a condition in which the capacity of the ER to fold proteins becomes saturated. IRE1 (inositol-requiring enzyme 1) and ATF6 (activating transcription factor 6) are two major sensors of unfolded proteins inside of the cells and are currently understood to be key transducers of UPR. Credle et al., Proc Natl Acad Sci USA 102, 18773-18748 (2005); Nadanaka et al., Mol. Cell. Biology 27, 1027-1043 (2007).

These metabolic pathways are activated by a number of viral genes including: a) Human cytomegalovirus 27 kDa ER-resident type I membrane glycoprotein, within the short unique region 11 (US11), which targets major histocompatibility complex (MHC) class 1 molecules for dislocation from ER to cytosol; b) nonstructural protein NS4B encoded by Hepatitis C virus (HCV), which physically interacts with CREB-RP/ATF6β and activates ATF6 and IRE1 pathways by inducing XBP1 splicing. Zheng et al., J. Microbiology 43, 529-536 (2005); and c) Hepatitis B virus 17 kDa protein within the small open reading frame X gene (HBx), which is a multifunctional transcription activator that regulates a variety of cellular events such as cell cycle, survival, and apoptosis.

IRE1, an endogenous exonuclease, can modify X-box binding protein mRNA (XBP1) to form spliced XBP1 mRNA (XBP1s), which results in a translation frame-shift, the product of which activates increased protein secretion through UPR pathway. Tigges et al., Metab. Eng. 8, 264 (2006). Tigges et al. further disclose transfection of cells with XBP1 and XBP1s to increase secretory capacity for biopharmaceutical manufacturing of secreted protein therapeutics. Tigges et al. also teach that transient transfection with XBP1s plasmid and the genes encoding secreted embryonic alkaline phosphatase (hSEAP), the secreted hormone VEGF, or secreted α-amylase can result in protein production of hSEAP, VEGF, and α-amylase, respectively.

Recombinant proteins are produced by a variety of techniques, including culturing host cells on solid substrates, on suspended microcarriers, and, for anchorage-independent cell, in non-adherent suspension culture. Adherent cultures include culture on microcarriers that can be maintained in suspension. In a suspension culture of anchorage-independent cells, cells are not attached to a substrate, but instead are maintained in suspension in a nutrient-containing medium within a suitable reaction vessel.

Various suspension methods are utilized for the production and maintenance of particular host cells. Typical suspension cell culturing methods for microcarriers and for anchorage-independent cells use shakers, rollers, stirrers, or air-lift systems that agitate a cell culturing medium and cells in culture or in bioreactors. Aeration, temperature, rate of agitation and like conditions can be controlled and adjusted to provide conditions favorable to growth of the culture and high production of recombinant protein.

SUMMARY OF THE INVENTION

The invention takes advantage of certain unexpected findings with respect to the use of HBx to increase heterologous (recombinant) protein production by cell cultures of mammalian cells. In its various embodiments, the invention provides methods and compositions for producing recombinant protein by expressing HBx in mammalian host cells which also express a recombinant protein, whereby production of the recombinant protein is elevated in such cells in relation to comparable recombinant cells which do not express HBx.

In a first embodiment, the invention comprises a method of producing a heterologous protein in mammalian host cells, comprising growing mammalian host cells selected from the group consisting of HKB11 cells, CHO-S cells, BHK21 cells, C2C12 cells, and HEK293 cells, wherein said mammalian host cells contain a nucleic acid encoding HBx and a nucleic acid encoding the heterologous protein, under conditions such that HBx and the heterologous protein are expressed by the mammalian host cells.

In a further embodiment, the invention comprises a method of producing a heterologous protein in mammalian host cells comprising growing mammalian host cells in non-adherent suspension culture, wherein said mammalian host cells contain a nucleic acid encoding HBx and a nucleic acid encoding the heterologous protein, under conditions such that HBx and the heterologous protein are expressed by the mammalian host cells.

In a further embodiment, the invention comprises a method for producing a heterologous protein in mammalian host cells, comprising: a) providing mammalian host cells which contain nucleic acid encoding HBx and which contain nucleic acid providing exogenous XBP1s; and b) growing said mammalian cells under conditions such that HBx, exogenous XBP1s, and the heterologous protein are expressed by the mammalian cells. The effect of the coexpression of nucleic acids encoding HBx and heterologous XBP1s can be synergistic.

In another embodiment, the invention is a composition comprising mammalian host cells containing a nucleic acid encoding a heterologous protein and a nucleic acid encoding HBx, wherein the mammalian host cells are derived from a cell line selected from the group consisting of HKB11 cells, CHO-S cells, BHK21 cells, and HEK293 cells, and wherein the cells express or can be induced to express HBx and the heterologous protein.

In another embodiment, the invention is a composition comprising a suspension culture of anchorage-independent mammalian host cells, which mammalian host cells contain nucleic acid encoding HBx and nucleic acid encoding a heterologous protein, and which mammalian host cells express or can be induced to express HBx and the heterologous protein.

In another embodiment, the invention is composition comprising mammalian host cells, which mammalian host cells contain nucleic acid encoding HBx, nucleic acid which provides exogenous XBP1s, and nucleic acid encoding a heterologous protein, wherein the mammalian host cells express or can be induced to express HBx, exogenous XBP1s and the heterologous protein.

In a further embodiment, the invention is a stably transfected cell line obtained from one of the aforementioned compositions, for example, a clone which is isolated from the composition of mammalian cells (e.g. a high-producing clone) and used to found a new culture or other population of mammalian cells based on such clone.

DESCRIPTION OF PREFERRED EMBODIMENTS

Figure 1:
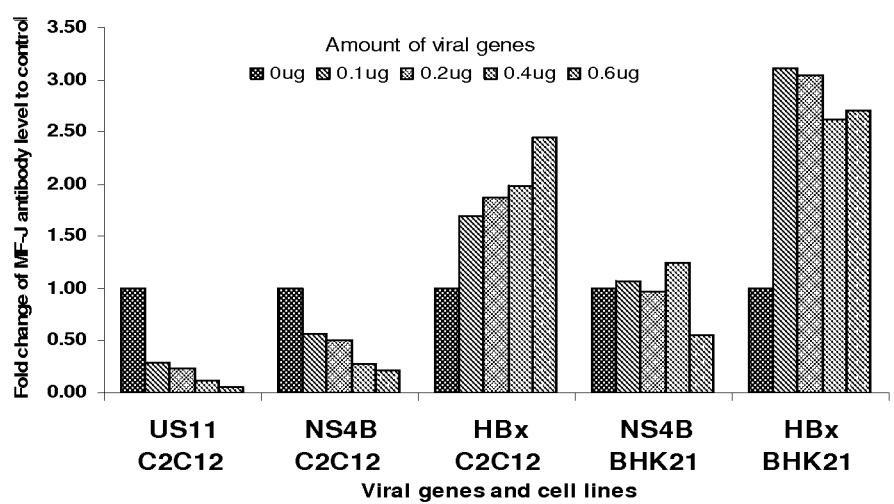
FIG. 1 illustrates the effect of transient transfection by graduated amounts of three viral genes, as shown, on the production of secreted MF-J antibody in C2C12 and BHK21 host cell lines.

The terms "comprising" and "having" are used in an open and inclusive manner.

Cultured cells useful for commercial-scale production of proteins, such as therapeutic proteins, generally have properties that include a stable phenotype, well-defined nutrient requirements, the ability to glycosylate proteins appropriately, and a lack of infectious viruses. Several mammalian host cells and lines have been characterized in this manner and are useful in the context of the present invention.

Host cell types include HKB11 cells—a somatic cell fusion between human kidney and human B cells, CHO-S cells—a Chinese hamster ovary cell line, BHK21—a baby hamster kidney cell line, and HEK293 cells—a human embryonic kidney cell line. Cells adapted for anchorage-dependent growth (i.e. surface-adherent) and those adapted for growth in suspension are useful in various embodiments. In some embodiments, anchorage-independent suspension culture-adapted cells are utilized. In other embodiments, only certain mammalian host cells, namely HKB11, CHO-S, BHK21, and HEK293 cells, and recombinant forms thereof, are included. In connection with different embodiments, other production cells can also be used, including CHO cells, FRhL-2, MRC-5 diploid fibroblasts, SP2/0—a murine myeloma, and NS0—also a murine myeloma.

In general, cell culture of recombinant mammalian host cells is known to those skilled in the art of recombinant protein production, and unless otherwise specified in connection with a particular embodiment of the invention, any form of cell culture is contemplated by the invention.

In a particular embodiment, the invention includes within its scope the use of host cells in anchorage-dependent culture, the cells of which culture are prepared by any method of introducing nucleic acid into the host cells whereby the nucleic acid is expressed to produce a recombinant protein within said anchorage-dependent cell culture.

Suspension cell culture of recombinant host cells is also known to those skilled in the art of recombinant protein production, and, in one embodiment, any form of suspension culture of anchorage-independent cells is contemplated by the invention. In this particular embodiment, the invention includes within its scope the use of host cells in anchorage-independent suspension culture prepared by any method of introducing nucleic acid into a host cell whereby the nucleic acid is expressed to produce a recombinant protein within said anchorage-independent suspension culture.

Methods of introducing nucleic acid into cells include but are not limited to transfection with virus or incomplete virus, incorporation of plasmids, and gene gun.

A "heterologous protein" generally means a protein other than the product of XBP1 or XBP1s, unless indicated otherwise herein. A heterologous protein is one not normally associated with, or naturally expressed by, the host cell, including one that is introduced by transfer of exogenous nucleic acid into the cell.

The notation XBP1/XBP1s denotes XBP1, XBP1s, or both XBP1 and XBP1s. While the invention should not be limited by putative mechanisms of action, it is currently understood that XBP1 is expressed to form an mRNA that is spliced by the host cell to form XBP1s (i.e. spliced XBP1) mRNA, which is translated into a protein that regulates cell function. Some authors designate unspliced XBP1 as XBP1u. The term "nucleic acid providing XBP1s" specifically includes any nucleic acid that, when transfected into a host cell and expressed, increases the level of XBP1s. Such a nucleic acid is inherently exogenous. Nucleic acid encoding XBP1s is preferred, in one embodiment. In other embodiments, nucleic acid encoding XBP1 (unspliced) is included, with the proviso that IRE1 is not rate-limiting in the cell. Moreover, the combination of nucleic acids encoding XBP1 and IRE1 is encompassed. Also included is a nucleic acid having a regulatory element that enhances expression of XBP1s. In the embodiments of the invention involving providing XBP1s in the host cells, therefore, the XBP1s may be provided in a form which either expresses a precursor transcript which is spliced in situ or in a form expresses an XBP1s transcript which does not require splicing.

The nucleic acids transfected into the host cell can be expressed transiently or stably. In one embodiment, stable expression by the host cells of heterologous XBP1s occurs. In another embodiment, stable expression of HBx by the host cells occurs. In yet another embodiment, stable expression of the heterologous protein by the host cells which also stably express HBx and/or XBP1s occurs.

Alternatively, the host cells may transiently express HBx and/or XBP1s, and/or the heterologous protein.

The nucleic acid encoding HBx and the heterologous product protein can be introduced into the host cells on separate vectors or as different cassettes on the same vector, using methodology familiar to persons skilled in the art, and transfected cells can be identified using appropriate selection.

The nucleic acid encoding HBx and the nucleic acid encoding the heterologous product protein can be introduced into the host cell at the same time, at substantially the same time or, optionally, at different times, and in either sequence.

The nucleic acid encoding HBx, XBP1 or XBP1s, and the heterologous product protein can be introduced into the host cell on separate vectors or as different cassettes on the same vector, using methodology familiar to persons skilled in the art.

The nucleic acids encoding HBx, XBP1/XBP1s, and the heterologous product protein can be introduced into the host cell at substantially the same time or, optionally, at substantially different times, and in any sequence. In one embodiment, the host cell is transfected with nucleic acid encoding XBP1s. Regulatory elements may be adjusted to optimize conditions for industrial scale production. Expression of HBx, XBP1s, and the heterologous protein can occur constitutively or under inducible conditions. Under inducible conditions, gene expression can be induced in response to an exogenous agent. Such agents can include, but are not limited to, tetracycline (Baron et al., Methods Enzymol. 327:401 (2000)), edysone (Pollock et al., Curr Opin Biotechnol. 13:459 (2002)), rapamycin (No et al., Proc Natl Acad Sci USA 93:3346 (1996)), and mifepristone (Nordstrom, Curr Opin Biotechnol. 13:453 (2002)).

In some embodiments, the nucleic acid encoding HBx and/or the nucleic acid encoding XBP1 or XBP1s are introduced into a precursor cell that expresses the product protein.

In other embodiments, the nucleic acid encoding the heterologous product protein is introduced into a precursor cell that expresses HBx and/or XBP1/XBP1s.

Moreover, the nucleic acid encoding HBx and the nucleic acid encoding XBP1 or XBP1s can be introduced into a precursor cell that is a transgenic mammalian cell expressing said heterologous protein.

The HBx gene sequence can be obtained from Genebank, e.g. AM282986. Alternatively, the HBx gene can be obtained from any strain, genotype or subgenotype of Hepatitis B virus, provided that the HBx gene thereof encodes a functional X protein and has, or can be modified to contain, any restriction enzyme sites which may be necessary for manipulation into expression vectors as contemplated herein. Strains, genotypes and subgenotypes of Hepatitis B virus are described in, for example, Hayashi et al., J. Med. Virology 79: 366-373 (2007).

XBP1 nucleic acid and XBP1s nucleic acid are available to workers in the art and examples are identified under the following accession numbers:

| | Accession Number | |
| --- | --- | --- |
| Species | XBP1 | XBP1s (spliced) |
| Mus musculus | AF 027963 | AF 443192 |
| Homo sapiens | AB 076383 | AB 076384 |
| Rattus norvegicus | XM 214067 | — |
| Gallus gallus | XM 415209 | — |
| Drosophila melanogaster | NM 079983 | NM 166427 |
| Bos taurus | BC 102639 | — |

The XBP1 nucleic acid may be of any origin, but is in some embodiments of human or murine origin. In one embodiment, the nucleic acid encoding XBP1s may encode a precursor (XBP1, containing the intron) which is readily processed in situ by the host cell to create the spliced form (XBP1s). The exonuclease IRE1 present in the host cells removes a 26 bp intron from XBP1 transcripts, resulting in a translation frameshift that renders the XBP1s protein transcriptionally active. Therefore, recombinant XBP1s can be produced by transfecting a host cell with a nucleic acid encoding the precursor. Alternatively, the nucleic acid may encode a transcript which lacks the intron and directly encodes the spliced form.

In some embodiments, the methods of the present invention involve suspension culturing the host cells, and in some embodiments suspension culturing of anchorage-independent cells. By "suspension culturing of anchorage-independent cells" or "non-adherent suspension culture," it is meant culturing of a recombinant cell culture in which the cells are substantially non-adherent to any substrate within the culture. By "substantially non-adherent" is meant that less than 10%, and in some embodiments is less than 5%, of the cells adhere to a surface (e.g. walls) of the culture vessel after one hour, two hours or longer of culture. Adherence can be measured, for example, by comparison of non-adherent cells to total cell yield upon gentle swirling in trypsin-free, calcium-free and magnesium-free medium, or, in another embodiment, in trypsin-containing medium. In one aspect, the suspension culture of the host cells occurs in a bioreactor system in which the cells may be maintained as substantially non-adherent cells during the production of recombinant protein. The suspended cells can be agitated by methods known in the art, including air lift and stirring, or by rotation or swirling the bioreactor container.

Equipment and procedures for carrying out anchorage-independent suspension cell culture are familiar to the skilled artisan and are disclosed, for example, in U.S. Pat. Nos. 7,294,484; 7,157,276; 6,660,501; and 6,627,426, the disclosure of each of which is incorporated by reference. In general, principles, protocols, equipment, and practical techniques for anchorage-independent suspension cell culture can be found in Chu et al., Industrial choices for protein production by large-scale cell culture, 2001, Curr Opin Biotechnol. 12, 180-7; Warnock et al., Bioreactor systems for the production of biopharmaceuticals from animal cells, 2006, Biotechnol Appl Biochem. 45, 1-12, which are incorporated herein by reference.

It is contemplated that any mammalian host cell that can be adapted to, and maintained in, an anchorage-independent suspension cell culture and transfected with HBx to increase protein production can be used in accordance with the methods of the invention. Specific examples of host cells are DG44, Chinese hamster ovary (CHO cells) cells, simian fibroblast CV-1 cells transformed by SV40 deficient in origin of replication region (COS cells), and human cell lines (HEK 293, CEM). Mouse, dog, and stem cell lines are also contemplated. Currently, in some embodiments cells lines include suspension-adapted versions of DG44, CHO, CV-1, COS, and HEK 293 cells. A specific type of DG44 cells may be DG44sus cells. Means for adapting adherent cells to growth in non-adherent suspension culture are familiar to the skilled artisan.

In some aspects of the invention, the host cells have a non-hepatocyte origin. For example, the cells can preferably be kidney cells, ovarian cells, lymphocytes, Kupffer cells, somatic fusion cells, stem cells, or any other cell of non-hepatocyte origin.

Any cell culture medium compatible with, and capable of sustaining, mammalian host cells is suitable. Choice of cell culture media depends on the particular recombinant system and determination of suitable media is not critical and can be readily made by the skilled person. Suitable culture media include MEM, DME-high glucose, DME-low glucose, Iscove's MDME, Medium 199, McCoy's, Ham's F10, Ham's F12, RPMI 1640, NCTC-109, and L-15 (Leibovitz). Moreover, mixtures of culture media can be used, e.g. DME/F12 or DME/M199. Specialized media, not limited to AthenaES™ Cell Culture Media BRFF-BMZERO™, BRFF-EPM2™, BRFF-HPC1™ and BRFF-P4-8F™ can also be used. Cell growth may be achieved without serum. Cell growth may also be achieved without animal products. In the case of recombinant therapeutic proteins intended for human administration, no animal products are used at any stage of media preparation and use. For the production of therapeutic proteins, the medium can be free of serum- and/or animal-derived protein, examples of which media are disclosed, for example, in U.S. Pat. Nos. 5,804,420 and 7,094,574; WO 97/05240; and EP 0 872 487.

FreeStyle™ (Invitrogen, Carlsbad, Calif.) is a useful cell culture medium containing no components of animal origin, and which is therefore desirable for use in connection with expressing proteins intended for use as human therapeutics.

In some aspects, the cell culture medium may have a reduced effective concentration of calcium. That is, the free calcium concentration may be less than that of the corresponding standard medium by about 50%, by 60%, by 70%, by 80% or by at least 90%. In one embodiment, reduced calcium media are used with anchorage-independent suspension cultures.

In other aspects, the culture medium for cell culture may be used with an atmosphere of air or preferably air containing $CO_2$, e.g. 5-10% (vol/vol) in air.

Culture of anchorage-independent cells in suspension reduces the physical space required to produce biological protein products. Anchorage-independent-adherent suspension culture also has advantages in bioproduction. Conditions of the anchorage-independent suspension culture can be adjusted to optimize recombinant protein production based on the particular type of host cells and the recombinant protein being produced.

Mammalian cell culture is useful for expression of human biological proteins for research and for clinical use. In some embodiments, BHK21 or HKB11 cells that express HBx have enhanced expression of a heterologous product protein. The DG44sus host cells are useful as a host cell in connection with the suspension culture embodiment of the present invention in which HBx-transfected cells demonstrate enhanced production of a heterologous product protein in anchorage-independent suspension culture of recombinant mammalian cells. In yet another embodiment, human HKB11 cells that express HBx and heterologous XBP1s allow an increase, and in some embodiments a synergistic increase, in the production of a heterologous product protein.

Generally, a suitable expression vector for introduction of the heterologous gene into the mammalian host cells is a vector that provides control or regulatory sequences operably linked with the nucleic acid sequence encoding the heterologous gene. The regulatory sequences are capable of directing the expression of the heterologous gene in the host cell, either constitutively or inducibly. Suitable vectors and regulatory sequences are well known to those of skill in the art.

For example, suitable vectors can be, or contain components from, viral vectors selected from simian virus SV40, retroviruses, bovine papilloma virus, vaccinia virus, and adenovirus, or commonly used bacterial vectors or commonly used insect and/or mammalian expression vectors, or integrative vectors which lead to a stable cell line expressing the recombinant protein product.

Methods for introduction of a vector such as a plasmid into mammalian cells are well known. Examples of suitable methods include, without limitation, dextran-mediated transfection, calcium phosphate precipitation, polybrene mediated transfection, protoplast fusion, electroporation, encapsulation of the polynucleotide(s) in liposomes, viral transduction and direct microinjection of the DNA into nuclei. Moreover, references that provide details of transfection methods include: Wigler et al., Cell 14:725, 1978; Corsaro and Pearson, Somatic Cell Genetics 7:603, 1981; Graham and Van der Eb, Virology 52:456, 1973; Neumann et al., EMBO J. 1:841-5, 1982; Hawley-Nelson et al., Focus 15:73, 1993; Ciccarone et al., Focus 15:80, 1993; Miller and Rosman, BioTechniques 7:980-90, 1989; and Wang and Finer, Nature Med. 2:714-6, 1996, the disclosure of each of which is incorporated herein by reference. Production of recombinant polypeptides in cultured mammalian cells is disclosed in U.S. Pat. Nos. 4,713,339; 4,784,950; 4,579,821; and 4,656,134, among others, the disclosure of which is incorporated herein by reference.

The methods of the present invention encompass, in some embodiments, use of a nucleic acid expression construct that encodes the product protein in a vector that comprises one or more promoter sequences. The promoter may or may not be, in nature, associated with the particular coding sequence. In some embodiments, the nucleic acid encoding HBx and the nucleic acid encoding the heterologous product protein are operably linked to a promoter so as to cause the host cell to express the heterologous protein product and, in some embodiments, secrete the protein product into the culture media. Suitable promoters are known to the skilled artisan and include strong, constitutive promoters such as CMV promoter. It is also contemplated to use an inducible promoter known in the art.

Sequences which contain selectable markers may also be transfected into the cell line. These markers may be contained on the vector containing the heterologous protein, or may be separately transfected using conventional techniques, such as those described herein. Selectable markers for mammalian cells are known in the art, and include for example, thymidine kinase, aminoglycoside phosphotransferase, hydromycin B phosphotransferase, asparagine synthetase, and adenosine deaminase. Other markers may be readily selected by one of skill in the art, as desired.

In some embodiments, host cells are a fast growing cell line with improved ease of transfection or transduction, or other desired quality, which can be transfected with HBx and nucleic acid encoding a heterologous protein.

Product proteins of the invention can include food proteins, especially food proteins supplying essential nutrients, proteins for use in drug development or analysis, food processing proteins, and therapeutic proteins. The product proteins can be secretory or non-secretory. Secretory proteins are suitable due to their ease of recovery. In some embodiments, therapeutic proteins produced as secreted products are particularly suitable. Variants of product proteins can be produced (i.e. mutant versions of the protein which retain all or a part of the function of the wild type protein, such as, for example, the B-domain deleted variants of human coagulation Factor VIII).

Therapeutic proteins useful in the present invention include, without limitation, proteins normally found in blood such as blood factors; proteins found in blood in response to stress, infection, or disease; proteins found in mammalian milk; proteins normally found in lymph; proteins found in lymph in response to stress, infection, or disease; proteins normally found in cerebro-spinal fluid; proteins found in cerebro-spinal fluid in response to stress, infection, or disease; proteins normally found in the gut; or proteins from microorganisms; or muteins of these proteins. Moreover, the therapeutic proteins can be mutated, such as by truncation or deletion of parts such as one or more domains. Moreover, muteins can comprise one, two, three, or more amino acid substitutions. In some embodiments, amino acid substitutions are conservative, as understood in the art.

A "therapeutic protein" or "therapeutic polypeptide" refers to a polypeptide possessing biological activity, or a precursor thereof, that can be used for the prevention and/or treatment of disease. Examples of therapeutic polypeptides include those capable of preventing, inhibiting, stabilizing or reversing an inherited or noninherited genetic defect in metabolism, immune regulation, hormonal regulation, enzymatic defect, or membrane associated structural function. For example, therapeutic protein can replace an absent or defective cellular protein or enzyme, or supplement production of a defective or low expression cellular protein or enzyme. Therapeutic proteins can include fusion proteins, antibodies, antibody fragments, and antibody mimetics, and shuffled protein variants with enhanced activities.

The therapeutic proteins can include coagulation factors, antibodies, virus antigens, bacterial antigens, fungal antigens, protozoal antigens, and metabolic regulators. The metabolic regulators can include peptide hormones, chemokines, cytokines, and growth factors. In certain embodiments therapeutic proteins can be tumor suppressors, cytokines, pro-apoptotic factors, or proteins derived from microorganisms.

The term "blood protein" refers to one or more proteins, or biologically active fragments thereof, found in normal human blood, including, without limitation, hemoglobin, α-1-antitrypsin, fibrinogen, human serum albumin, prothrombin/thrombin, antibodies, blood coagulation factors, and biologically active fragments thereof. Coagulation proteins include Factor V, Factor VI, Factor VII, Factor VIII and derivatives thereof such as B-domain deleted FVIII, Factor IX, Factor X, Factor XI, Factor XII, Factor XIII, Fletcher Factor, Fitzgerald Factor, and von Willebrand Factor.

The term "milk protein" refers to one or more proteins, or biologically active fragments thereof, found in normal human milk, including casein, lactoferrin, lysozyme, α-1 antitrypsin, antibodies, protein factors, immune molecules, and biologically active fragments thereof.

In some embodiments, when the therapeutic protein is an antibody, any nucleic acid encoding such antibody is contemplated. Included are monoclonal antibodies, single chain antibodies, antibody fragments, chimeric antibodies, humanized antibodies, and other antibody variant molecules which can be produced in recombinant adherent or suspension cell culture.

Antibodies within the scope of the present invention include, but are not limited to: cetuximab, rituximab, trastuzumab, gemtuzumab, alemtuzumab, ibritumomab, tositumomab, bevacizumab, alemtuzumab, HuPAM4, 3F8, G250, HuHMFG1, Hu3S193, hA20, SGN-30, RAV12, daclizumab, basiliximab, abciximab, palivizumab, infliximab, eculizumab, omalizumab, efalizumab, panitumumab, anti-HER2 antibodies (Carter et al., Proc. Natl. Acad. Sci. USA, 89:4285-4289 (1992), U.S. Pat. No. 5,725,856); anti-CD20 antibodies such as chimeric anti-CD20 "C2B8" as in U.S. Pat. No. 5,736,137; a chimeric or humanized variant of the 2H7 antibody as in U.S. Pat. No. 5,721,108, B1; or anti-IL-8 (St John et al., Chest, 103:932 (1993), WO 95/23865); anti-VEGF antibodies including humanized and/or affinity matured anti-VEGF antibodies such as the humanized anti-VEGF antibody huA4.6.1 AVASTIN™ (Kim et al., Growth Factors, 7:53-64 (1992), WO 96/30046, and WO 98/45331); anti-PSCA antibodies (WO01/40309); anti-CD40 antibodies, including S2C6 and humanized variants thereof (WO00/75348); anti-CD11a (U.S. Pat. No. 5,622,700, WO 98/23761, Steppe et al., Transplant Intl. 4:3-7 (1991), and Hourmant et al., Transplantation 58:377-380 (1994)); anti-IgE (Presta et al., J. Immunol. 151:2623-2632 (1993), WO 95/19181); anti-CD18 (U.S. Pat. No. 5,622,700 or WO 97/26912); anti-IgE (including E25, E26 and E27; U.S. Pat. No. 5,714,338 or U.S. Pat. No. 5,091,313, WO 93/04173 or PCT/US98/13410, U.S. Pat. No. 5,714,338); anti-Apo-2 receptor antibody (WO 98/51793); anti-TNF-α, antibodies including cA2 (REMICADE™), CDP571 and MAK-195 (See, U.S. Pat. No. 5,672,347, Lorenz et al., J. Immunol. 156(4):1646-1653 (1996), and Dhainaut et al., Crit. Care Med. 23(9):1461-1469 (1995)); anti-Tissue Factor (TF) (European Patent No. 0 420 937 B1); anti-human $α_4β_7$ integrin (WO 98/06248); anti-EGFR (chimerized or humanized 225 antibody as in WO 96/40210); anti-CD3 antibodies such as OKT3 (U.S. Pat. No. 4,515,893); anti-CD25 or anti-tac antibodies such as CHI-621 (SIMULECT™) and (ZENAPAX™) (See U.S. Pat. No. 5,693,762); anti-CD4 antibodies such as the cM-7412 antibody (Choy et al., Arthritis Rheum 39(1):52-56 (1996)); anti-CD52 antibodies such as CAMPATH-1H (Riechmann et al., Nature 332:323-337 (1988)); anti-Fc receptor antibodies such as the M22 antibody directed against FcγRI as in Graziano et al., J. Immunol. 155(10):4996-5002 (1995); anti-carcinoembryonic antigen (CEA) antibodies such as hMN-14 (Sharkey et al., Cancer Res. 55(23Suppl): 5935s-5945s (1995); antibodies directed against breast epithelial cells including huBrE-3, hu-Mc 3 and CHL6 (Ceriani et al., Cancer Res. 55(23): 5852s-5856s (1995); and Richman et al., Cancer Res. 55(23 Supp): 5916s-5920s (1995)); antibodies that bind to colon carcinoma cells such as C242 (Litton et al., Eur J. Immunol. 26(1):1-9 (1996)); anti-CD38 antibodies, e.g. AT 13/5 (Ellis et al., J. Immunol. 155(2):925-937 (1995)); anti-CD33 antibodies such as Hu M195 (Jurcic et al., Cancer Res 55(23 Suppl): 5908s-5910s (1995) and CMA-676 or CDP771; anti-CD22 antibodies such as LL2 or LymphoCide (Juweid et al., Cancer Res 55(23 Suppl):5899s-5907s (1995)); anti-EpCAM antibodies such as 17-1A (PANOREX™); anti-GpIIb/IIIa antibodies such as abciximab or c7E3 Fab (REOPRO™); anti-RSV antibodies such as MEDI-493 (SYNAGIS™); anti-CMV antibodies such as PROTOVIR™; anti-HIV antibodies such as PRO542; anti-hepatitis antibodies such as the anti-Hep B antibody OSTAVIR™; anti-CA 125 antibody OvaRex; anti-idiotypic GD3 epitope antibody BEC2; anti-αv.γ3 antibody VITAXIN™; anti-human renal cell carcinoma antibody such as ch-G250; ING-1; anti-human 17-1A antibody (3622W94); anti-human colorectal tumor antibody (A33); anti-human melanoma antibody R24 directed against GD3 ganglioside; anti-human squamous-cell carcinoma (SF-25); and anti-human leukocyte antigen (HLA) antibodies such as Smart ID10; the anti-HLA DR antibody Oncolym (Lym-1) or adalimumab, or active fragments thereof. The preferred target antigens for the antibody herein are: HER2 receptor, VEGF, IgE, CD20, CD11a, and CD40.

When the therapeutic protein is a metabolic regulator, any protein or polypeptide metabolic regulator is contemplated. It will be understood that any mutant or variant of a therapeutic protein may be expressed using the method of the present invention.

By way of a non-limiting example, such therapeutic proteins include erythropoietin, human growth hormone, granulocyte colony stimulating factor, interferons-α, -x2b, -β, -β1a, -β1b and -γ, Factor IX, follicle stimulating hormone, interleukin-2, erythropoietin, anti-TNF-α, and a lysosomal hydrolase. The therapeutic proteins can also include vascular endothelial growth factor (VEGF), fibroblast growth factors (FGF, FGF1, FGF2, and FGF5), epidermal growth factor (EGF), platelet-derived growth factor (PDGF), nerve cell growth factor (NGF) and hepatocyte growth factor (HGF)).

When the therapeutic protein is a cytokine, any cytokine is contemplated. In specific embodiments, the cytokine is GM-CSF, G-CSF, IL-1α, IL-10, IL-2, IL-3, IL-4, IL-5, IL-6, IL-7, IL-8, IL-9, IL-10, IL-11, IL-12, IL-13, IL-14, IL-15, IL-16, IL-17, IL-18, IL-19, IL-20, IL-21, IL-22, IL-23, IL-25, IL-26, IL-27, IL-28, IL-29, IL-30, IL-31, IL-32 IFN-α, IFN-β, IFN-γ, MIP-1α, MIP-1β, TNF-β, TNF-α, TNF-β, keratinocyte growth factor, TGF-α, TGF-β, VEGF, or MDA-7.

Other proteins and polypeptides in which can be produced in accordance with the present invention include, but are not limited to, insulin, motilin, gastrin, prolactin, adrenocorticotropic hormone (ACTH), erythropoietin, growth hormone (GH), stem cell factor (SCF), thrombopoietin, osteoprotegerin (OPG), and obesity protein, granulocyte colony-stimulating factor (G-CSF), insulin-like growth factors (IGFs), macrophage colony stimulating factor (M-CSF), granulocyte macrophage colony stimulating factor (GM-CSF), colony simulating growth factors (CSFs), thyroid stimulating hormone (TSH), luteinizing hormone (LH), follicle stimulating hormone (FSH), human chorionic gonadotropin (HCG), neurotrophic growth factor (NGF), neurotrophic factor 3 (NT3), neurotrophic factor 4 (NT4), brain-derived neurotrophic factor (BDNF), glial cell line derived neurotrophic factor (GDNF), bone morphogenetic protein (BMP), megakaryocyte growth differentiation factor (MGDF), superoxide dismutase (SOD), tissue plasminogen activator (TPA), urokinase, streptokinase, kallikrein, α-galactosidase, pancreatic RNAse, platelet activating factor acetylhydrolase, interleukin-1 receptor antagonist (IL-1ra), REMICADE (Infliximab: a monoclonal antibody that blocks the biological activity of circulating TNFα), α-1 anti-trypsin, anti-angiogenesis agents, calcitonin and analogs, chemokines, enkephalins and other opioid peptides, glucagon, granisetron, growth hormone antagonist peptides, IgE suppressors, insulinotropin and analogs, luteinizing hormone, luteinizing hormone releasing hormone and analogs, parathyroid hormone and analog peptides, parathyroid hormone antagonist peptides, recombinant soluble receptors, tissue plasminogen activators, therapeutic antigens, and ENBREL (etanercept: dimeric fusion protein consisting of the extracellular ligand-binding portion of the human 75 kilodalton (p 75) tumor necrosis factor receptor (TNFR) linked to Fc portion of human IgG1).

When the therapeutic protein is a tumor suppressor, any tumor suppressor is contemplated. In specific embodiments, the nucleic acid encoding the tumor suppressor is APC, CYLD, HIN-1, KRAS2b, p16, p19, p21, p27, p27mt, p53, p57, p73, PTEN, MDA-7, Rb, Uteroglobin, Skp2, BRCA-1, BRCA-2, CHK2, CDKN2A, DCC, DPC4, MADR2/JV18, MEN1, MEN2, MTS1, NF1, NF2, VHL, WRN, WT1, CFTR, C-CAM, CTS-1, zac1, ras, MMAC1, FCC, MCC, FUS1, Gene 26 (CACNA2D2), PL6, Beta* (BLU), Luca-1 (HYAL1), Luca-2 (HYAL2), 123F2 (RASSF1), 101F6, Gene 21 (NPRL2), or a gene encoding a SEM A3 polypeptide.

Glycoprotein IIb/IIIa platelet membrane receptor antagonist antibody, recombinant hirudin and thrombin, thrombin inhibitors such as Angiomax, angiopeptin, fibroblast growth factor (FGF) antagonist peptides, and monoclonal antibodies such as those specific for Platelet-Derived Growth Factor (PDGF) receptors, super oxide dismutases, super oxide dismutase mimetic, and combinations thereof are contemplated.

Suitable vaccine antigens include those of (including but not limited to subunit protein, peptide and toxoids), diphtheria, tetanus, HIB, Lyme disease, meningococcus, mumps, rubella, varicella, yellow fever, respiratory syncytial virus, tick borne Japanese encephalitis, pneumococcus, streptococcus, typhoid, influenza, hepatitis, including hepatitis A, B, C and *E. otitis* media, rabies, polio, parainfluenza, rotavirus, Epstein Barr Virus, CMV, chlamydia, non-typeable haemophilus, moraxella catarrhalis, human papilloma virus, tuberculosis including BCG, gonorrhea, asthma, atherosclerosis, malaria, *E. coli*, Alzheimer's Disease, salmonella, diabetes, cancer, herpes simplex, human papilloma, HIV-1, HIV-2, SIV, FIV, FeLV, Equine infectious adenovirus, anemia virus, eastern equine encephalitis virus, western equine encephalitis virus, Venezuelan equine encephalitis virus, rift valley fever virus, Crimean-Congo hemorrhagic fever virus, SARS coronavirus, monkey pox virus, adenovirus, smallpox, Japanese (mosquito borne) encephalitis, yellow fever, Dengue, West Nile encephalitis, enterotoxigenic *E. coli, Campylobacter H. pylori, C. difficile*, and measles. The protein can be the adenovirus death protein.

When the therapeutic protein is a pro-apoptotic factor, any nucleic acid encoding such factors is contemplated. In some embodiments, the pro-apoptotic factor nucleic acid is CD95, caspase-3, Bax, Bag-1, CRADD, TSSC3, bax, hid, Bak, MKP-7, PARP, bad, bcl-2, MST1, bbc3, Sax, BIK, or BID.

In some embodiments, the therapeutic protein is derived from microorganisms. While any protein from a microorganism is contemplated, in some embodiments the proteins are antigens derived from viruses, bacteria, fungi, or protozoa.

The antigen can also be derived are selected from *Mycobacterium tuberculosis, Yersinia pestis, Rickettsia prowazekii, Rickettsia typhi, Rickettsia rickettsii, Ehrlichia*

*chaffeensis, Francisella tularensis, Bacillus anthracis, Helicobacter pylori* and *Borrelia burgdorferi.*

In some embodiments, the microorganism from which the antigens are derived are selected from the list of *Plasmodium falciparum, Plasmodium vivax, Plasmodium ovate, Plasmodium malariae,* and *Giadaria intestinalis.*

In some embodiments, the microorganism from which the antigens are derived are selected from the list of *Histoplasma, Ciccidis, Immitis, Aspergillus, Actinomyces, Blastomyces, Candida* and *Streptomyces.*

The trypsin-chymotrypsin family (S1) includes such members as: trypsin (forms I, II, III, IV, Va and Vb); trypsin-like enzyme; hepsin; TMPRSS2; venombin; cercarial elastase; brachyurin; Factor C; Proclotting enzyme; easter gene product; snake gene product; stubble gene product; Vitellin-degrading endopeptidase; hypodermin C; Serine proteases 1 and 2; achelase; chymotrypsin (forms A, B, II, and 2); Proteinase RVV-V (forms α and γ); flavoboxin; venombin A; Crotalase; enteropeptidase; acrosin; ancrod; seminin; semenogelase; tissue kallikrein; renal kallikrein; submandibular kallikrein; 7S nerve growth factor (chains α and γ); epidermal growth factor-binding protein (forms 1, 2, and 3); tonin; arginine esterase; pancreatic elastase I; pancreatic elastase 11 (forms A and B); pancreatic endopeptidase E (forms A and B); leukocyte elastase; medullasin; azurocidin; cathepsin G; proteinase 3 (myeloblastin); chymase (forms I and II); γ-renin; tryptase (forms 1, 2, and 3); granzyme A; natural killer cell protease 1; gilatoxin; granzymes B, C, D, E, F, G and Y; carboxypeptidase A complex component III; complement factors D, B, I; complement components C1r, C1s, and C2; calcium-dependent serine protease; hypodermin A, B, and C; haptoglobin (forms 1 and 2); haptoglobin-related protein; plasmin; apolipoprotein (a); hepatocyte growth factor; medullasin; thrombin; t-plasminogen activator; u-plasminogen activator; salivary plasminogen activator; plasma kallikrein; coagulation factors VII, IX, X, XI, and XII; and proteins C and Z, as well as as-yet unidentified members. All trypsin-chymotrypsin family member proteins can be protein products of the invention.

Other product proteins of this invention include, without limitation, receptor ligands, enzymes, adhesion peptides, coagulation inhibitors or clot dissolving agents such as streptokinase and tissue plasminogen activator, matrix metalloproteinase inhibitors and tissue inhibitors of metalloproteinase, and combinations of any of the foregoing.

Lysosomal hydrolases useful in the present invention include, but are not limited to, β-glucosidase, α-galactosidase-A, β-hexosaminidase, β-galactosidase, α-galactosidase, α-mannosidase, β-mannosidase, α-L-fucosidase, β-glucuronidase, α-glucosidase, α-N-acetylgalactosaminidase, and acid phosphatase.

Therapeutic antigens including all of the major polypeptide therapeutics such as agents for the common cold are also therapeutic proteins.

The methods and recombinant cell cultures of the invention can also comprise commercial proteins, for example those listed in Table 1.

TABLE 1

| Indication(s) | Commercial protein [generic name] |
|---|---|
| Renal Disorders, Cardiology Disorders, Arterial Vascular Disorders | Activase [Alteplase] |
| | Cathflo Activase [Alteplase] |
| | ReoPro [Abciximab] |
| | Retavase [Reteplase] |
| | Streptase [Streptokinase] |
| | TNKase [Tenecteplase] |
| Neurology Peripheral neuropathy (not intrinsically painful neuropathies) | Avonex [Interferon beta-1a] |
| | Betaseron [Interferon beta-1b] |
| | Botox [Botulinum Toxin Type A] |
| | Myobloc [Botulinum Toxin Type B] |
| | Rebif [Interferon beta-1a] |
| | Tysabri [Natalizumab] |
| Allergy, | Pulmozyme [Dornase alfa] |
| Pulmonary | Xolair [Omalizumab] |
| Rheumatology, | Enbrel [Etanercept] |
| Pain treatment (including peripheral neuropathies that are intrinsically painful) | Humira TM [Adalimumab] |
| | Kineret [Anakinra] |
| | Orencia [Abatacept] |
| | Remicade [Infliximab] |
| Gastrointestinal (includes non-viral hepatic disorders), | Aldurazyme [Laronidase] |
| | Fabrazyme [Agalsidase beta] |
| Genetic metabolic (inborn) disorders, Large volume parenterals | Naglazyme [Galsulfase] |
| Dental, | Alferon N Injection [Interferon alfa-n3] |
| Dermatology | Amevive [Alefacept] |
| | Raptiva [Efalizumab] |
| | Regranex [Becaplermin] |
| | Santyl [Collagenase] |
| Bacterial infectious disease, Sepsis, Ophthalmology | Xigris [Drotrecogin alfa (activated)] |
| Solid organ transplant, | Actimmune [Interferon gamma-1b] |
| Immunodeficiency white cell disorders, | Orthoclone [Muromonab-CD3] |
| Special pathogens (e.g., fungal, TB, Anthrax) | Simulect [Basiliximab] |
| | Zenapax [Daclizumab] |
| Viral infections (including viral hepatitis) | Copasys Copegus [Peginterferon alfa-2a] |
| | Infergen [Interferon alfacon-1] |
| | Intron A [Interferon alfa-2b] |
| | Pegasys [Peginterferon alfa-2a] |
| | Peg-Intron [Peginterferon alfa-2b] |
| | Roferon-A [Interferon alfa-2a] |
| | Synagis [Palivizumab] |

TABLE 1-continued

| Indication(s) | Commercial protein [generic name] |
|---|---|
| Biologic cancer treatments, | Avastin [Bevacizumab] |
| Biologic cancer ancillary treatments, | Bexxar [Tositumomab] |
| Graft versus Host Disease | Campath [Alemtuzumab] |
| | Elitek [Rasburicase] |
| | Elspar [Asparaginase] |
| | Eribitux [Cetuximab] |
| | Herceptin [Trastuzumab] |
| | Kepivance [Palifermin] |
| | Leukine [Sargramostim] |
| | Neulasta [Pegfilgrastim] |
| | Neumega [Oprelvekin] |
| | Neupogen [Filgrastim] |
| | Oncaspar [Pegaspargase] |
| | Ontak [Denileukin diftitox] |
| | Proleukin [Aldesleukin] |
| | Rituxan [Rituximab] |
| | Zevalin [Ibritumomab tiuxetan] |
| Diagnostic imaging, | Abbokinase [Urokinase] |
| Hematology, | Aranesp [Darbepoetin alfa] |
| Venous vascular disorders | CEA-Scan TM [Arcitumomab] |
| | Epogen [Epoetin alfa] |
| | NeutroSpec [Technetium fanolesomab] |
| | Procrit [Epoetin alfa] |
| | ProstaScint [Capromab Pendetide] |
| | Verluma [Nofetumomab] |

Nucleic acid, which encodes the aforementioned proteins, either is known in the art or can be obtained using methods familiar to the skilled artisan. For example, nucleic acids encoding high-affinity antibodies can be obtained by screening phage libraries.

The heterologous protein produced by the method of the invention can include a PRO polypeptide. The PRO polypeptide can lack an N-terminal signal sequence and/or the initiating methionine and can be encoded by a nucleotide sequence that encodes such an amino acid sequence. The method of the invention also encompasses production of PRE PRO polypeptides, that is, precursors of PRO polypeptides.

The heterologous protein produced by the method of the invention can be recovered by methods well known in the art, including lysis of cells to recover non-secreted proteins or isolation from the culture medium to obtain secreted proteins. Moreover, proteins can be purified by any useful means, including but not limited to precipitation, binding to ion-exchange or affinity resins or membranes, and size exclusion chromatography. General methods for expressing and recovering recombinant protein produced by a mammalian cell system are disclosed by, for example, Etcheverry, Expression of Engineered Proteins in Mammalian Cell Culture, in Protein Engineering: Principles and Practice, Cleland et al. (eds.), pages 163 (Wiley-Liss, Inc. 1996).

In some embodiments, the production level of therapeutic protein may be about 1.1×, 1.2×, 1.4×, 1.6×, 1.8×, 2×, 2.2×, 2.4×, 2.6×, 2.8×, 3×, 3.2×, 3.4×, 3.6×, 3.8×, 4×, 4.2×, 4.4×, 4.6×, 4.8×, 5×, or more, or any range derivable therein, as compared to the production level in other cells not transfected with HBx or with HBx and XBP1s.

Methods of the invention can comprise a specific amount of produced heterologous protein. In some embodiments, the amount of therapeutic protein produced per liter of cell culture non-adherent suspension may be about 1, 2, 3, 4, 5, 6, 7, 8, 9, 10, 11, 12, 13, 14, 15, 16, 18, or 20 mg or potentially higher, or any range or combination derivable therein. Thus, compositions of the invention include such amount of therapeutic protein, which may or may not be further purified. The harvested heterologous protein or proteins recovered from the non-adherent suspension culture may be further purified by means known in the art. Purification may involve any method known in the art, including but not limited to concentration, diafiltration by tangential flow ultrafiltration, chromatography or size resolution purification, affinity purification, and ion exchange chromatography. In some embodiments, chromatography may be employed in heterologous protein purification. In some embodiments, the chromatography may be affinity chromatography or ion exchange chromatography. In still other embodiments heterologous protein purified by affinity chromatography may be further subjected to ion-exchange chromatography. In some embodiments of the present invention, harvested heterologous protein may be subjected to size resolution purification. In some embodiments, the size resolution purification may involve a protein gel or size exclusion column. The heterologous protein made according to the invention can be formulated pharmaceutically with one or more carriers, excipients or the like and such formulations can be administered using customary methods.

EXAMPLES

Example 1

HBx but not US11 and NS4B Increases Protein Production in BHK21 Cells

Plasmid Construction

All transgenes used for transient transfection were cloned into the expression vector pZac2.1 (Gene Therapy Program, Penn Vector core, University of Pennsylvania) that contains a full-length human CMV promoter, a Promega chimeric intron, MCS (multiple cloning site) and a SV40 polyA (Gene Therapy Program).

HBx gene was obtained from an HBV strain ADW2 genome contained in a pBS plasmid. In the plasmid, HBx was flanked by MluI and XbaI restriction sites and was amplified by PCR using two primers (forward primer GER270: GAT-CACGCGTGCCACCATGGCTGCTAGGCTG, SEQ ID NO. 1 and reverse primer GER271: GTCGACTCTAGATT-AGGCAGAGGTGAAAAAGTTG, SEQ ID NO. 2). The amplified HBx was inserted into expression vector pZac2.1 to generate the pHBx plasmid.

The US11 gene of human CMV as described in Gretch and Stinski Virology, 174 (2) 522-532 (1990) was amplified by PCR using two primers (forward primer GER275: GAT-CACGCGTGCCACCATGAACCTTGTAATG, SEQ ID NO. 3 and reverse primer GER276: GTCGACTCTAGATCAC-CACTGGTCCGAAAAC, SEQ ID NO. 4) and inserted into pZac2.1 to generate the plasmid pUS11.

The NS4B gene of HCV (Gene bank: M588335) was synthesized through Invitrogene (BlueHeron Biotechnology). The gene was flanked by MluI and XbaI and cloned into pZac2.1 to create the plasmid pNS4B.

A full-length human antibody MF-J (which binds specifically to human mesothelin) was used as a representative heterologous protein. In MF-J, the heavy chain and light chain are linked by a furin/2A cleavage site. In order to make final product of pMF-J/fu/2A for transient transfections, a template plasmid pMorphH.Fur2A.kappanlight (pGT149) was created. To construct pGT149, a BlpI site was eliminated from the human kappa constant region in pMORPH h Ig kappa 1 (HuCal technology from MorphoSys AG, Gemany) by digesting with BbvC1 and BlpI and ligating with annealed oligos GER212 (5'-TCAGCAGCACCCTGACCC-3') SEQ ID NO. 5 and GER213 (5'-TCAGGGTCAGGGTGCTGC-3') SEQ ID NO. 6. Then pGT149 was made by a three-fragment ligation. One fragment was pZac2.1 which had been backbone opened with NheI+NotI. The second fragment was a PCR product with oligos GER204 (5'-GGAGAC-CCAAGCTGGCTAGC-3', SEQ ID NO. 7) and GER205 (5'-ACGTCGCCGGCCAGCTTCAGCAGGTC-GAAGTTCAGGGTCTGCTTCACGGGGG CTCTCTTGGCCCGTTTACCCGGAGACAGGGAGAG-3', SEQ ID NO. 8) from pMORPH h IgG1-1 plasmid (containing the NheI site-VH leader-EcoRI/BlPI stuffer-hH constant-N term part of fur2A sequence ending in Ngo MIV) and digested with NheI and Ngo MIV. The third fragment also was a PCR product with oligos GER206 (5'-GAAGCTGGC-CGGCGACGTGGAGTCCAACCCCGGC-CCCATGGTGTTGCAGACC CAGGTC-3', SEQ ID NO. 9) and GER 207 (5'-ATCAGTGCGGCCGCCTAACACTCTC-CCCTGTTGAAGC-3', SEQ ID NO. 10) from pMORPH h Ig kappa 1 plasmid (lacking the BlpI site) (containing the Ngo-MIV C-term end of Fur2A seq-Vkappa leader-EcoRV/BsiWI stuffer-human kappa constant region-NotI fragment) and digested with NgoMIV and NotI.

To construct pMF-J/fu/2A, the MF-J antibody variable heavy (VH) and light chains (VL) were inserted into the pGT149 template by a four-way ligation since the antibody has Kappa light chains. MF-J VH and VL fragments were obtained from pMORPH9 MF-J by MfeI-BlpI or EcoRV-BsiWI digestion respectively. pGT149 was opened with EcoRI and BlpI as backbone. pGT149 was also digested with BlpI and EcoRV to obtain the middle fragment linking VH and VL.

A secreted Gaucissa luciferase gene ("Gluc" in the Figures) was obtained from pCMV-Gluc plasmid (Sigma, St. Louis, Mo.), and subcloned into pZac2.1 by restriction enzyme digestion of KpnI+NotI to generate pGluc.

The murine SEAP (secreted alkaline phosphatase) gene was excised by Sal I and Not I restriction enzymes from plasmid pGT36 (described in Szymanski et al, Molecular Therapy 15 (7) 1340-1347 (2007) and then subcloned into pZac2.1 opened with Not I and Sal I to create pmuSEAP plasmid.

Cell Culture

BHK21 cells were maintained in a growth medium supplemented with 5% fetal bovine serum, non-essential amino acids, and Na Pyruvate. HKB11 cells were maintained in a growth medium supplemented with 5% fetal bovine serum for adherent culture.

Transient Transfections

For co-transfection of pHBx with pMF-J/fu/2A or pGluc, both BHK21 and HKB11 cells were transiently transfected by the Fugene6 method (Roche, Indianapolis, Ind.). The cells were seeded into 12-well plates 24 h prior to transfection at a cell density of about $1.5 \times 10^5$ cells/well for BHK21 and about $2 \times 10^5$ cells/well for HKB11. For each transgene, six wells were transfected with different amounts of plasmid as shown in Table 2. The amount of target gene plasmid was kept constant while pHBx amount was varied. pBlueScript (pBS) was used to equilibrate the total amount DNA per well so that the transfection conditions were consistent between wells. The desired amount of DNA was mixed into 50 μl of opti-MEM with 4.8 μl Fugene6. Cell culture supernatants or cells were collected 96 hours later. Each experiment was repeated at least three times.

TABLE 2

| Well# | 1 | 2 | 3 | 4 | 5 | 6 |
|---|---|---|---|---|---|---|
| pTransgene (ug) | 0.5 | 0.5 | 0.5 | 0.5 | 0.5 | 0.5 |
| pHBx (ug) | 0 | 0.1 | 0.2 | 0.4 | 0.6 | 0.8 |
| pBS (ug) | 0.8 | 0.7 | 0.6 | 0.4 | 0.2 | 0 |

For single plasmid transfections with Fugene6 the DNA:Fugene6 ratio was kept at about 1:6 (0.8 μg DNA:4.8 μl Fugene6 per 12-well). If only pMF-J/fu/2A or pGluc was transfected into cells, then the plasmid was about 0.8 μg/well. Each transfection was performed in duplicate or triplicate and the group of transfections was repeated 2-3 times. If pHBx was transfected into cells, then pHBx amounts varied from about 0 μg-0.8 μg and pBS was used to control for the total amount DNA transfected per cell. The transfection procedure was the same as described above.

Detection of Full-Length Antibody MF-J/fu/2A by ELISA

Immulon 4 HBX plates were coated with 25 ng/50 μl/well mesothelin (c-terminal Flag tag, SEC pool, 1.41 mg/ml concentration in stock) in bicarbonate buffer overnight at 4° C. The plates were blocked for 1 hour with 200 μl/well Blocking Buffer (3% BSA in PBS) while shaking. Standard MF-J antibody (1.66 mg/ml) and samples were prepared as 50 μl/well within desired percentage of culture medium and incubated 2 hours at RT. The starting point of MF-J antibody standard curve was 1 μg/ml and then 1:3 serial dilution to total of 11 points. For cell culture supernatant, two to four dilution points for each sample were performed so that at least two points fell within the linear range of the standard curve. The plates were then washed 4 times with 0.05% PBST (0.05% TWEEN 20 in PBS buffer) washing buffer using plate-washer (Bio-tek). 50 μl/well of HRP-conjugated goat anti-human IgG (Pierce, 1:5000 dilution) were incubated at RT for 1 hour following four times washing with PBST (0.05% TWEEN). Absorbance at 405 nm was measured after 100 μl/well of ABTS (Sigma) addition. The antibody concentration of each sample was calculated by Softmax pro 4.3.1 software.

Secreted Gaussia luciferase (Gluc) Assay

Secreted Gluc activity was assayed by a *Renilla* luciferase kit (Promega, Madison, Wis.). Cell supernatants were diluted between $10^4$ and $10^5$ in 1× passive lysis buffer (Promega). 20 μl diluted sample was used for measurement. The results were expressed as relative light units (RLU).

muSEAP Activity Assay muSEAP activities were determined by a chemiluminescent activity assay kit (Applied Biosystems, Bedford, Mass.).

Western Blotting

Cells were lysed in RIPA buffer (Sigma, St. Louis, Mo.) or 1×LDS buffer (Invitrogen, Carlsbad, Calif.). The lysis material was then loaded and separated on 12% Bis-Tris gel (Invitrogen, Carlsbad, Calif.). The gel was blotted onto a nitrocellulose membrane through iBlot (Invitrogen, Carlsbad, Calif.) and immediately blocked in 5% milk in PBS at 4° C. overnight. The membrane was then incubated with Rabbit anti-human HBx polyclonal antibody (Abcam, Cambridge, Mass. 1:2000 in 0.05% PBST) at RT 2 hours followed HPR conjugated goat anti-rabbit IgG (Jackson Labs, 1:5000 in 0.05% PBST) for another hour. The bands were detected using ECL Plus (Amersham Biosciences, Pittsburgh, Pa.).

The effect of three viral genes on protein production was screened in a transient transfection manner in a number of different cell lines. Increasing amounts of pUS11, pNS4B and pHBx expressing plasmids were co-transfected with a constant amount of pMF-J/fu/2A (0.5 μg) into C2C12 and BHK21 (FIG. 1). The supernatants were collected after 96 hours of culture. Functional full-length antibody MF-J expression level was detected by ELISA. Fold change was calculated as the ratio of protein expression to a control well having 0.5 μg of target gene plasmid but without viral genes addition. The results presented in FIG. 1 illustrate that expression of HBx, but not expression of US11 or NS4B, increases protein production by about 2-3 fold in both C2C12 and BHK2 cells. The US11 gene in CHO-K1 cells and the NS4B gene in CHO-S and HKB11 cells were tested with co-expression of MF-J antibody or secreted Gluc. Neither US11 nor NS4B were observed to increase protein production in these cell lines.

Example 2

Transient Co-Transfection of Target Genes with HBx Enhances Protein Production in Production Cell Lines BHK21 and HKB11

Figure 2:
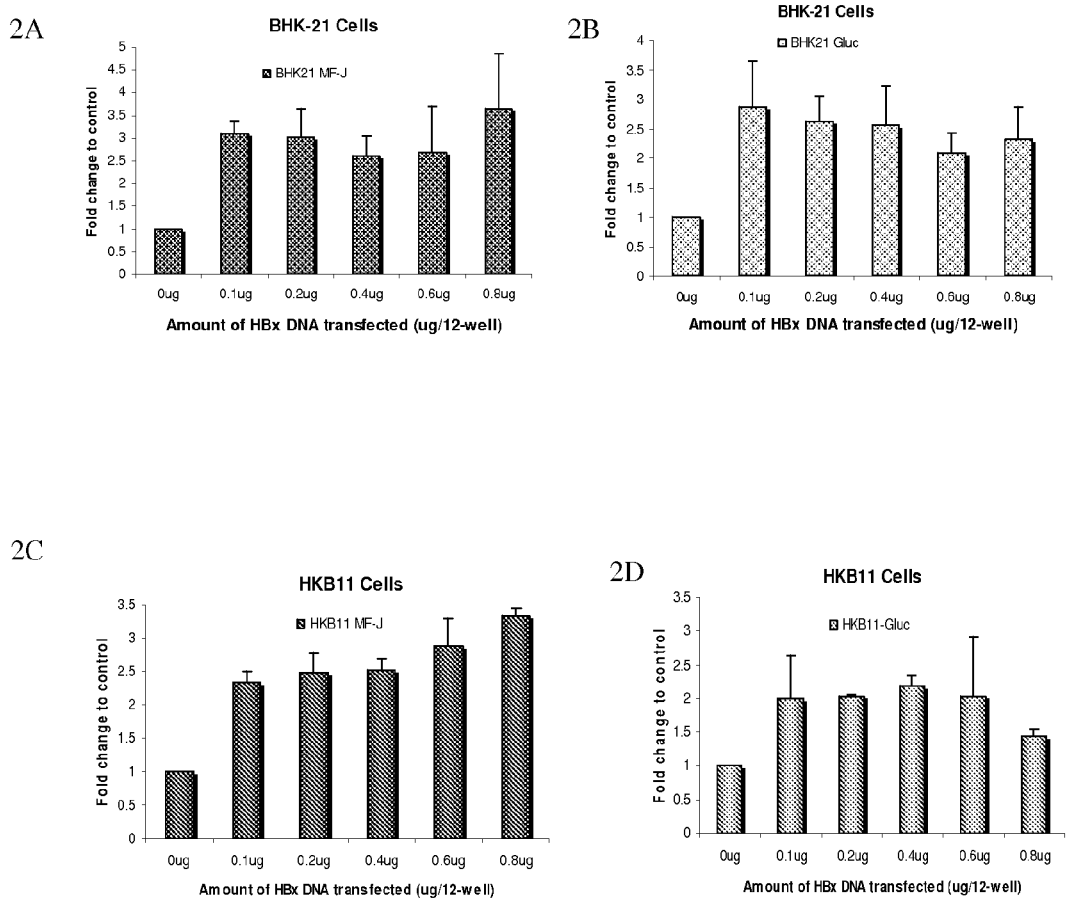
FIG. 2 illustrates increases in secreted MF-J antibody or luciferase (Gluc) production obtained upon transient transfection of recombinant BHK21 and HBK11 cells with graduated amounts of nucleic acid encoding HBx.

The effect of HBx on protein production was further evaluated in a transient transfection format in certain mammalian host cell lines. Increasing amounts of pHBx expressing plasmid were co-transfected with a constant amount of pMF-J/fu/2A or pGluc into BHK21 and HKB11 cells (FIG. 2). The cells were lysed at 96 hours post-transfection and a western blot analysis was performed to confirm that HBx was expressed in a dose-dependent manner. FIG. 2 shows the result with BHK21 cells. Similar results were seen in HKB11 cells. Similar results were seen in HKB11 cells.

Western blot analysis of HBx expression in BHK21 cells transiently co-transfected with pMF-J/fu/2A was performed. A whole cell extract was separated on 12% Bis-Tris gel and probed with anti-human HBx antibody. An equal amount of protein was loaded in each lane. A 17.5 kDa band was observed in all transfected wells but not the control well. The amount of HBx expressed increased in approximately monotonic fashion for 0.1 to 0.8 μg pHBx used for transfection.

Example 3

Transient Co-Infection with HBx Increases Protein Production

Supernatants were also collected at 96 hours from the same samples as used for the Western blot analysis in Example 2. The results revealed that co-transfection of HBx with MF-J Ab resulted in a 2.5-3.5 fold increase of MF-J antibody expression over a wide range of pHBx:pMF-J ratios (from 0.2:1 to 1.6:1) in both BHK21 and HKB11 cells (FIGS. 2A and 2C). Co-transfection of HBx with the reporter gene Gluc caused a 1.5-2.5 fold increase of Gluc expression in both BHK21 and HKB11 cells.

FIG. 2 illustrates that HBx enhances protein production in transient co-transfection. BHK21 (2A and 2B) and HKB11 (2C and 2D) cells were co-transfected with increasing amount of pHBx and a fixed amount (0.5 μg) of either pMF-J/fu/2A full-length antibody (2A and 2C) or a reporter gene, pGluc (2B and 2D). Protein production secreted into the supernatant medium was measured 96 hours later by ELISA for MF-J antibody (2A and 2C) or a *Renilla* luciferase kit for Gluc (2B and 2D). Fold change was calculated as the ratio of protein expression to a control well with 0.5 μg of target gene plasmid but without HBx addition. The graphs represent the average of three experiments.

Example 4

Transient Co-Transfection of Target Genes with HBx Increased Protein Production in C2C12 Cells The effect of HBx on protein expression was also evaluated in mouse skeletal muscle C2C12 cells. Again a range of pHBx plasmid (amounts from 0-0.8 μg) was co-transfected with 0.5 μg of pMF-J/fu/2A, pGluc or pmuSEAP. Data presented in FIG. 3 show that HBx enhances protein expression in C2C12 cells with a wide range of pHBx: pTransgene ratios (from 0.05:1 to 1.6:1).

Figure 3:
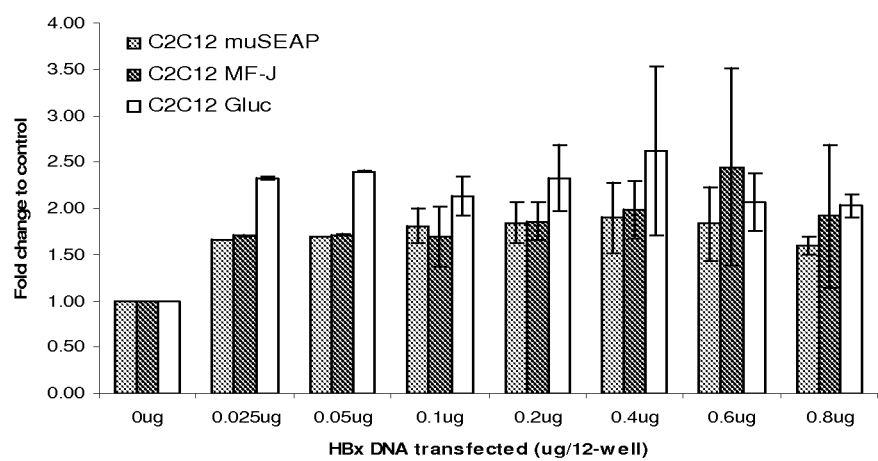
FIG. 3 illustrates production of secreted embryonic alkaline phosphatase, secreted antibody, or luciferase from recombinant C2C12 skeletal muscle cells transiently transfected with graduated amounts of nucleic acid encoding HBx.

FIG. 3 illustrates that HBx enhances protein production in transient co-transfection in C2C12 cells. C2C12 cells were co-transfected with constitutively-expressed HBx and MF-J full-length antibody or reporter genes Gluc or muSEAP. Protein production from supernatant was measured 96 hours later by ELISA for MF-J antibody, *Renilla* luciferase kit for secreted Gluc activity, or SEAP kit for secreted muSEAP activity. Fold change was calculated as the ratio of protein expression to a control well with 0.5 μg of target gene plasmid but without HBx addition. The graphs in FIG. 3 represent the average of three experiments.

Thus, co-expression of HBx with heterologous nucleic acid can significantly enhance the yield of the product protein in certain host cells and host cell lines.

Example 5

Expression of HBx in Stable Pools of BHK21 and HKB11 Cells

Lentivirus Production

In order to make HBx lentivirus, HBx gene was excised with NheI and NotI from pHBx and subcloned into lentiviral vector pCDH1-MCS1-EF1-Puro (System Biosciences, Mountain View, Calif.) to form pCDH1-HBx plasmid. This plasmid has a minimal CMV promoter. 293 T cells are seeded at a density of $6 \times 10^6$ cells in growth media (DMEM+10% FBS+1×L-glutamine) in a 15 cm dish incubated at 37° C. and 5% $CO_2$. The next day the media is aspirated and replaced with the transfection media containing opti-MEM (Invitrogen) containing plasmids pLP1 (encoding gag-pol; Invitrogen), pLP2 (encoding rev; Invitrogen) and pLP (encoding VSV-G; Invitrogen), the gene transfer plasmid (encoding the HBx protein) and lipofectamine 2000 reagent (Invitrogen). The transfection media is replaced after 24 hours with the maintenance media (DMEM+5% FBS+1×L-glutamine). Forty-eight hours after transfection, the media is collected, filtered using a Millex-HV 0.45 μm PVDF filters (Millipore) and virus particles are concentrated by ultracentrifugation.

Establishment of Stable Pools and Clones

To generate HBx-bearing pools and clones, BHK21 and HKB11 cells were seeded in 6-well plates with $1 \times 10^6$ cells/well the day before the lentiviral transduction. 200 μl of lentivirus with multiplicity of infection (MOI) of 0.1, 1 and 10 were added to the cells. After 4 hours of incubation, the medium containing lentivirus was removed and the cells were washed with fresh medium 2-3 times before adding the final 2 ml of culture medium. Puromycin was added to the cells 48 hours later at a concentration of 2 μg/ml for BHK21 and 2.5 to 5 μg/ml for HKB11.

For single clones, the pooled cells were seeded at 1 cell/well and 0.1 cell/well in 96-well plates using 100 μl medium containing selection drug in each well. After about 1-2 weeks of incubation, the cells were expanded into 24-well plates when 80-90% confluence was reached. Clones were then either frozen or grown for further analysis.

BHK21 and HKB11 cells were transduced with Lenti-HBx (lentivirus expressing full-length HBx) at MOIs of 0.1, 1 and 10. The stable pools were the blend of cells after puromycin selection from its corresponding MOI. The HBx expression level in BHK21 and HKB11 pools were evidenced by western blot. HBx expression levels increased when MOIs of viruses were increased.

The whole cell extract was separated on 12% Bis-Tris gel and probed with anti-human HBx antibody. An equal amount of protein was loaded in each lane. Western blot analysis of HBx expression in BHK21 and HKB11 stable pools revealed no expression in control transfections and graduated increasing expression of 17.5 kDa HBx with 0.1, 1.0, and 10 MOI of Lenti-HBx.

Example 6

Protein Production Increases in HBx-Expression Stable Pools

Figure 4:
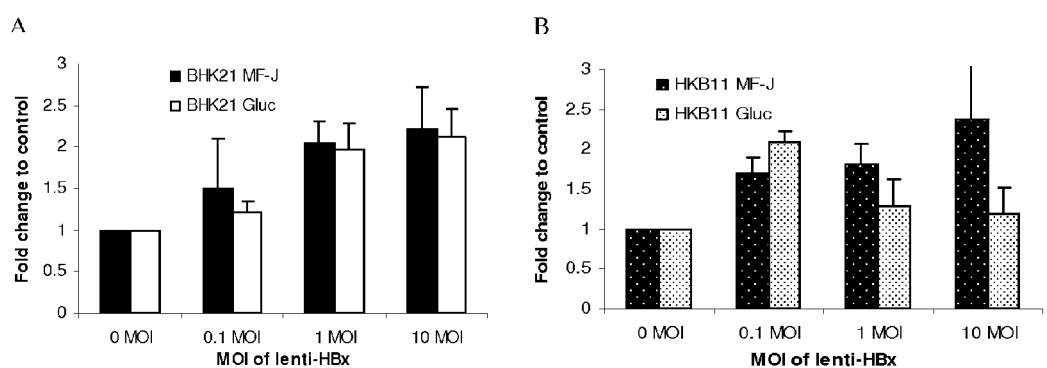
FIG. 4 illustrates production of secreted antibody or luciferase in BHK21 cell pools (panel A) and HKB11 cell pools (panel B) stably transfected with HBx.

Stable HBx pools were used in the pilot experiment to assess an overall representation and average effect of HBx on the cell productivity. pMF-J/fu/2A and pGluc were transiently transfected into the BHK21 and HKB11 stable pools expressing different levels of HBx. As shown in FIG. 4, both BHK21/HBx and HKB11/HBx pools yield more than a 2-fold increase of protein production.

FIG. 4 illustrates that protein production was increased in BHK21 and HKB11 stable pools constitutively expressing HBx. BHK21/HBx and HKB11/HBx stable pools were transfected with pMF-J/fu/2A or pGluc in 12-well plates. Supernatants were collected 96 hours later. MF-J antibody level and Gluc activity were measured by ELISA and *Renilla* luciferase kit respectively. Fold change was calculated as the ratio to parental control cells.

Example 7

Creation of Stable BHK21/HBx and HKB11/HBx Clones

Figure 5:
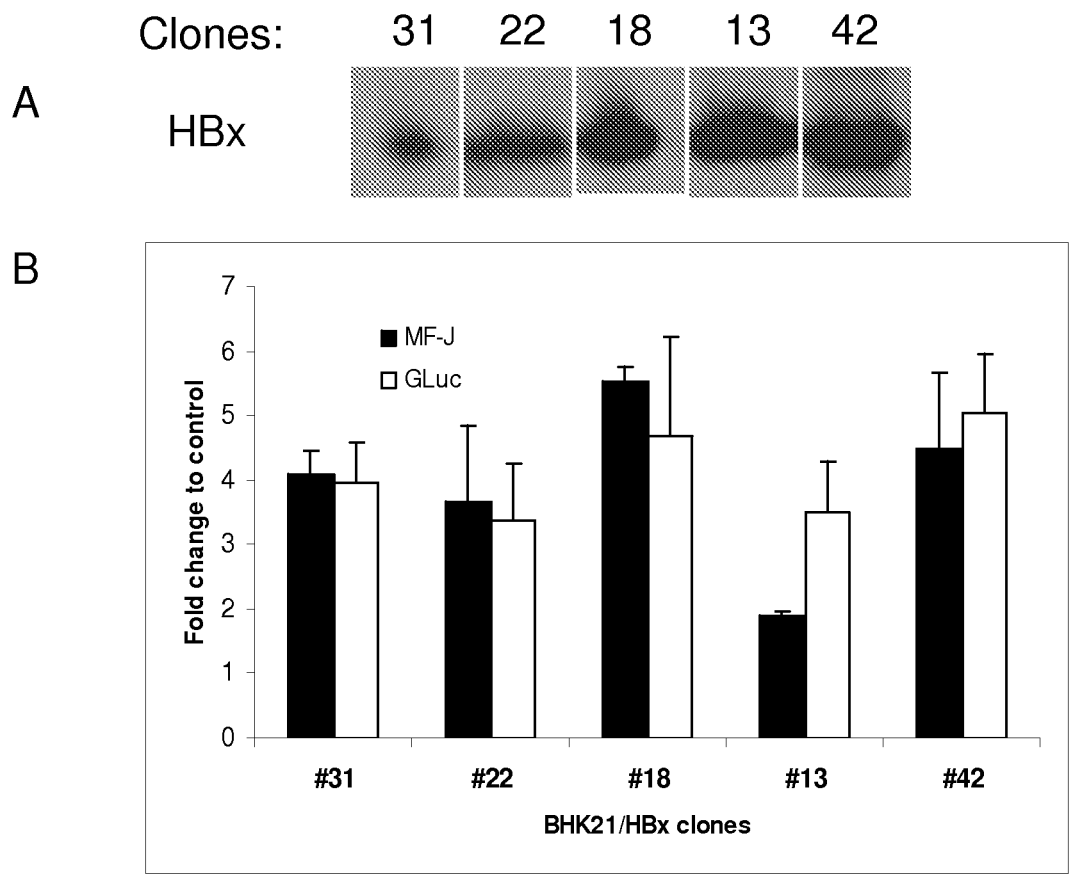
FIG. 5 illustrates HBx expression (panel A) and production of secreted antibody or luciferase (panel B), in five BHK21 clones stably transfected with HBx: clones 21, 22, 18, 13, and 42.

From three stable pools (MOIs of 0.1, 1, and 10), cells were plated into 96-well plates at a cell concentration of 0.1 cell/well and 1 cell/well with 100 μl of growth medium under puromycin selection. A total of 42 clones were isolated. Twenty-four (24) clones were further evaluated for HBx expression level and protein productivity. No obvious correlation between HBx expression level and protein productivity was observed. Accordingly, five clones were then selected based upon different levels of HBx expression (low, medium and high) and comparable levels of MF-J and Gluc expression. The clones had the following apparent HBx expression: clone 31, low; clone 22, medium; clone 18, high; clone 13, high; and clone 42, high. As shown in FIG. 5, these BHK21/HBx clones can increase MF-J antibody and Gluc reporter gene protein production by about 2 to over 5 fold.

FIG. 5 illustrates that protein production was increased in BHK21 stable clones constitutively expressing HBx. For a Western blot of HBx protein from various clones, $3 \times 10^6$ cells from each clone were lysed in 300 μl of 1×LDS sample buffer, heated and sonicated. 30 μl ($3 \times 10^5$ cells) was loaded on each lane, separated on 12% Bis-Tris gel and probed with anti-human HBx antibody. FIG. 5 shows BHK21/HBx stable clones which were transfected with pMF-J/fu/2A or pGluc in 12-well plates. Supernatants were collected 96 hours later. MF-J antibody level and Gluc activity were measured by ELISA and *Renilla* luciferase kit respectively. Fold change was calculated as the ratio to parental control cells.

Thus, certain cell lines engineered to stably express HBx can increase the yield of heterologous product protein.

Example 8

The Effect of Non-adherent DG44sus Suspension vs. Adherent DG44 Cells on Protein Production in Transient Co-Transfection of Target Genes with HBx The DG44 cell line is a dihydrofolate reductase (DHFR)-deficient cell line derived from CHO pro3-cells. Urlaub et al., 1983, Cell, 33:405-12 (1983). The DG44 cell line was adapted to non-adherent suspension culture to make the DG44sus line. The effect of HBx on protein expression was evaluated in both cell lines. DG44 and DG44sus cells were co-transfected with a range of pHBx plasmid from 0-0.8 μg and with 0.5 μg of pGluc. Protein production from supernatant was measured 72 hours later by *Renilla* luciferase kit for secreted Gluc activity. Fold change was calculated as the ratio of protein expression to a control well with 0.5 μg of target gene plasmid but without HBx addition. The graphs represent the average of three experiments.

Figure 6:
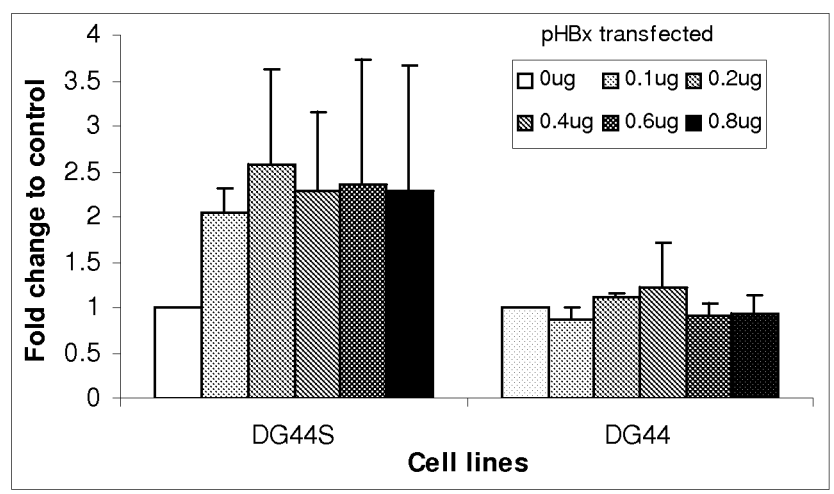
FIG. 6 illustrates luciferase production in transiently transfected anchorage-dependent ovarian (DG44) cells and transiently transfected anchorage-independent suspension culture-adapted ovarian (DG44sus) cells in relation to non-transfected cells.

FIG. 6 shows that HBx can increase Gluc expression 2-2.5 fold in DG44sus cells (labeled "DG44s") but not in DG44 adherent cells. This increase indicates that even in cell lines of the same origin, the cell culture situation (non-adherent suspension vs. adherent) can have an effect on protein production.

Example 9

The Effect of 293F Suspension vs. HEK293 Adherent Cells on Protein Production in Transient Co-Transfection of Target Genes with Hbx The effect of HBx on protein expression was also evaluated in a HEK293 cell line and a 293F cell line (Invitrogen). A range of pHBx plasmid from 0-0.8 μg was co-transfected with 0.5 μg of pGluc or pMF-J. Protein production from supernatant was measured 72 hours later by *Renilla* luciferase kit for secreted Gluc activity and by ELISA for secreted MF-J antibody. Fold change was calculated as the ratio of protein expression to a control well with 0.5 μg of target gene plasmid but without HBx addition. The graphs represent the average of two-three experiments.

Figure 10:
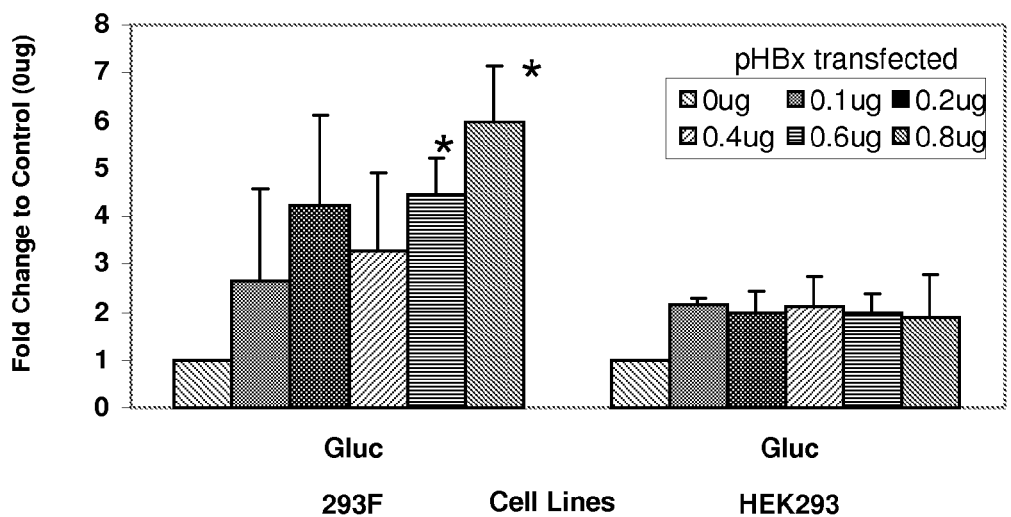
FIG. 10 illustrates luciferase production in transiently transfected HEK293 cell line and transiently transfected an anchorage-independent suspension culture-adapted 293F cell line in relation to non-transfected cells.
Figure 10:
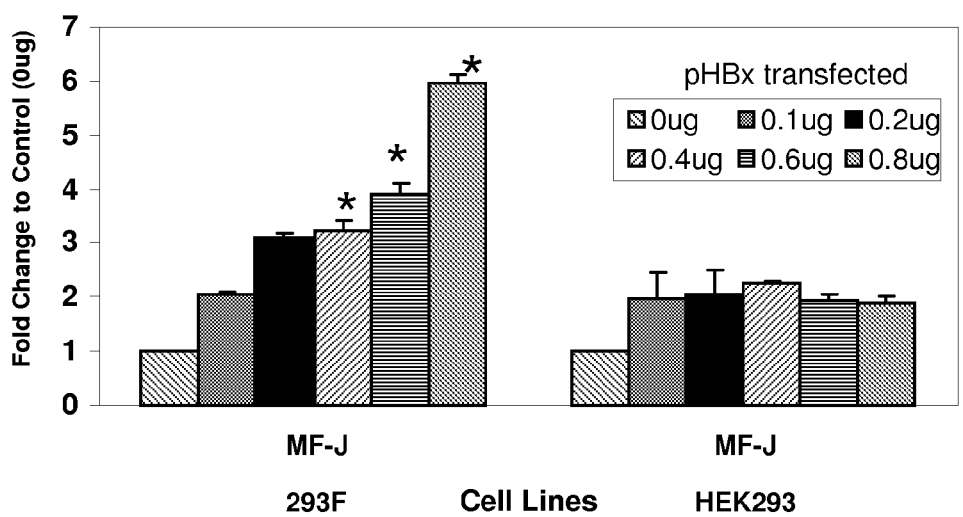

FIG. 10 shows that HBx can increase Gluc or MF-J antibody expression 2-6 fold in 293F suspension cells but about 2 fold in HEK293 adherent cells. This again indicates that even cell lines from the same origin, the cell culture situation (non-adherent suspension vs. adherent) can have an effect on protein production.

Example 10

HBx-Mediated Production Increase is Independent of Activation of XBP1

Figure 7:
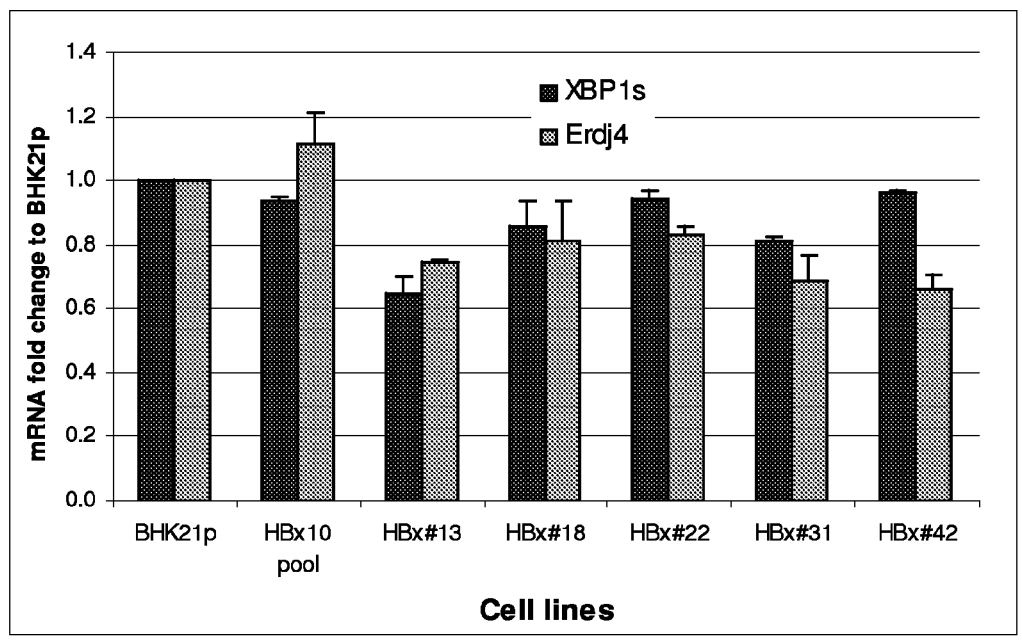
FIG. 7 illustrates expression of endogenous XBP1s and Erdj4 mRNA level in BHK21 parental (BHK21p), HBx10 pool, and five clones stably transfected with HBx: 13, 18, 22, 31, and 42.

The effect of the HBx-mediated protein production increase on activation of XBP1s was examined by measurement of XBP1s and its putative target Erdj4 mRNA by quantitative PCR (qRT-PCR). The data indicate that HBx does not induce XBP1s or its target Erdj4 mRNA level in this system. See FIG. 7. Total RNA was extracted and the same amount of total RNA was subjected to each reaction. GAPDH was used as an internal control. The fold change of mRNA level was calculated as the ratio to BHK21 parental cells (BHK21p). In addition, the XBP1s protein expression level in BHK21/HBx cell lines also showed no increase in comparison to BHK21 parental cells.

Example 10

Addition of XBP1s to BHK21/HBx Stable Cell Lines Increases Protein Production

The data presented here show that enhanced expression of XBP1s alone can increase heterologous protein expression in BHK21 parental cells by transient co-transfection (FIGS. 8A and 8B). The combinational engineering of HBx with XBP1s experiments were done in the same manner as shown in FIG. 3. A fixed amount of pMF-J/fu/2A or pGLuc, and graduated amounts of pXBP1s were transiently co-transfected into BHK21 parental cells, BHK21/HBx stable pools, and BHK21/HBx clones in 12-well plates. Protein expression levels in the supernatant medium was measured at 120 hours and are shown in FIGS. 8A (MF-J) and 8B (Gluc). With addition of XBP1s into BHK21/HBx stable cells, the BHK21/HBx/XBP1s cells yielded a more than 2.6 to 4.7 fold increase of MF-J and a 1.9 to 3.4 fold increase of Gluc compared with its corresponding BHK21/HBx pool and clones without addition of XBP1s. When using BHK21 parental cells transiently transfected with XBP1s as control, the BHK21/HBx/XBP1s cells yielded a more than 2.5 to 6 fold increase of MF-J antibody production and a 1.4 to 3.6 fold increase of Gluc production. These results demonstrate that XBP1s can further enhance protein production in BHK21/HBx stable transfectants compared with the cells transfected with either HBx or XBP1s alone.

Example 11

HBx and XBP1s Co-transfection Have a Synergistic Effect on Protein Production

Figure 8:
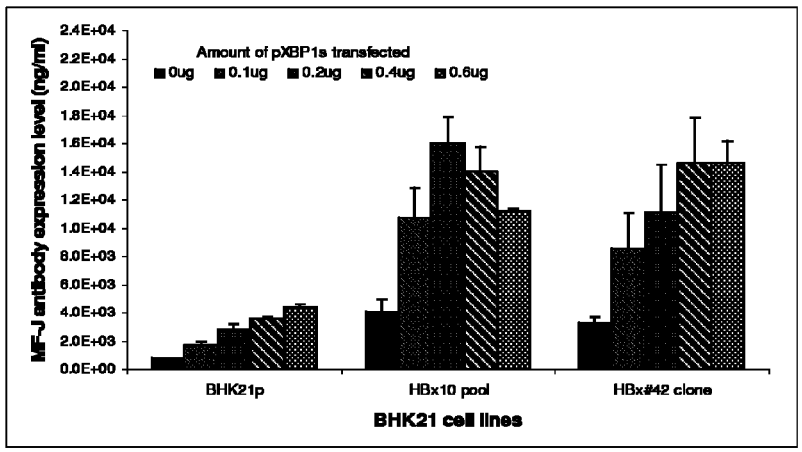
FIG. 8 illustrates production of two secreted product proteins by BHK21p, HBx10 pool cells, and either clone 42 or clone 22 of BHK21/HBx cells, each transfected with 0, 0.1 µg, 0.2 µg, 0.4 µg, or 0.6 µg, of pCMV-XBP1s per well. Panel A depicts MF-J antibody levels (ng/ml). Panel B depicts Gluc activity in relative light units (RLU).
Figure 8:
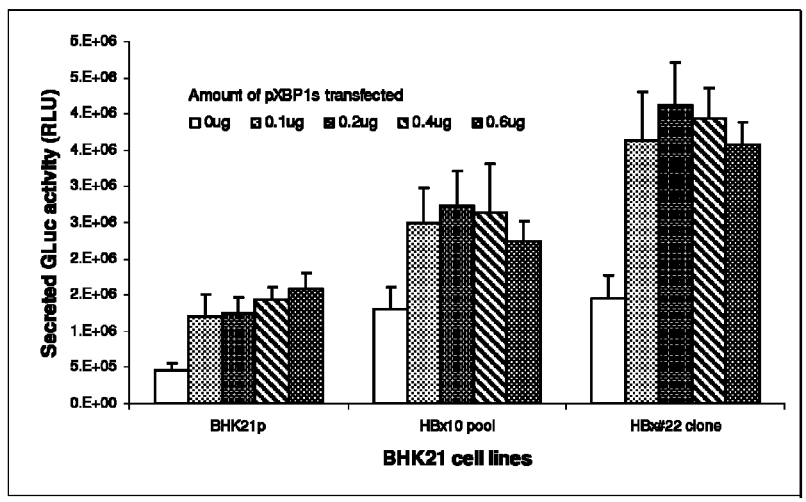

BHK21 parental cells were transiently transfected with either MF-J or Gluc in the absence of HBx or XBP1s to serve as controls for the experiment shown in FIG. 8. BHK21 parental cells and BHK21/HBx#22 clone were co-transfected with 0.2 μg of pXBP1s and either 0.5 μg of pMF-J/fu/2A full-length antibody or pGluc reporter gene in 12-well plates. Protein production from supernatant was measured 120 hours after transfection for MF-J by ELISA and 96 hours for GLuc activity by *Renilla* kit. Fold change was calculated as the ratio of protein expression to BHK21 parental cell with 0.5 μg of target gene plasmid but without HBx or XBP1s addition. The graphs illustrate the means and ranges of 2-4 experiments. These results illustrate that co-transfection with nucleic acid encoding HBx and XBP1s can elevate protein production in a synergistic manner in BHK21 cells.

Figure 9:
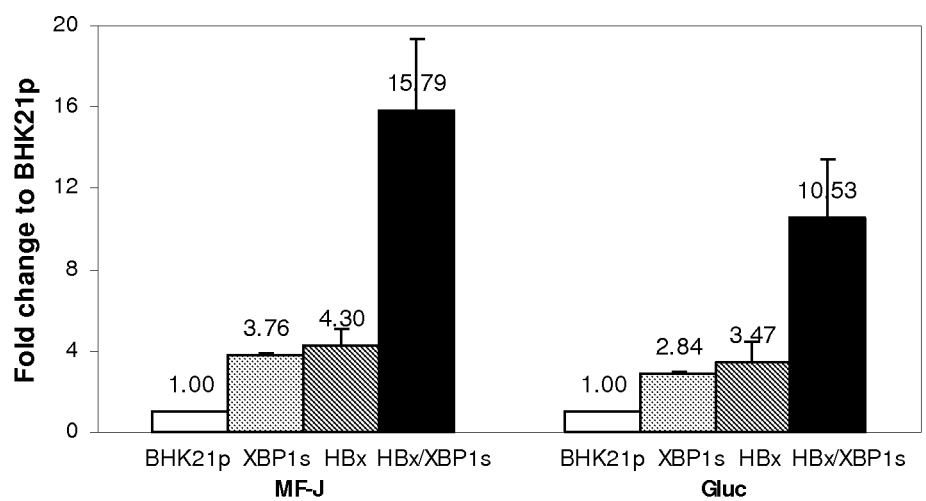
FIG. 9 illustrates the fold change of MF-J or Gluc production after XBP1s, HBx, expression alone or XBP1s and HBx co-expression, relative to BHK21p cells.

As shown in FIG. 9 for MF-J antibody expression, XBP1s addition alone at a pXBP1s dose of 0.2 μg yielded a 3.76 fold increase and HBx addition alone gave a 4.3 fold increase. When BHK21 cells were transfected with both HBx and XBP1s, a 15 fold MF-J antibody secretion was observed. Gluc expression was enhanced 2.84-fold by XBP1s transfection, 4.37-fold by HBx transfection and 10.53-fold by the co-transfection.

Table 3 shows, in greater detail, a comparison of the effects of HBx and XBP1s nucleic acids independently and together using BHK21 parental cells as a control. The enhancement of product protein production holds true in both BHK21/HBx pooled stables and clones (Table 3). The stable pools of cells show that the effect does not result from cloning. According to these measurements, co-expression of HBx and XBP1s has a synergistic effect on protein production in BHK21 cells. See Table 3. For example, BHK21/HBx#22/XBP1s cells reached its maximum Gluc protein production at a pXBP1s dose of 0.4 μg to 0.6 μg, while BHK21/HBx#42 cells reached its maximum Gluc protein production at a pXBP1s dose of 0.1 μg.

TABLE 3

| Cell Lines | pXBP1s | 0 μg | 0.1 μg | 0.2 μg | 0.4 μg | 0.6 μg |
|---|---|---|---|---|---|---|
| BHK21 parental | MF-J | 1.00 | 2.32 ± 0.08 | 3.76 ± 0.14 | 4.78 ± 0.14 | 5.86 ± 0.05 |
| BHK21/HBx10 pool | | 5.39 ± 0.05 | 14.25 ± 1.62 | 21.22 ± 3.07 | 18.70 ± 3.99 | 14.94 ± 2.21 |
| BHK21/HBx#22 | | 4.30 ± 0.84 | 11.36 ± 3.13 | 15.79 ± 3.54 | 16.39 ± 2.70 | 18.39 ± 0.32 |
| BHK21/HBx#42 | | 4.48 ± 1.26 | 11.41 ± 2.38 | 14.87 ± 2.77 | 19.39 ± 1.53 | 19.38 ± 1.19 |
| BHK21 parental | Gluc | 1.00 | 2.60 ± 0.16 | 2.84 ± 0.16 | 3.36 ± 0.34 | 3.74 ± 0.49 |
| BHK21/HBx10 pool | | 2.98 ± 0.71 | 5.92 ± 1.65 | 6.52 ± 1.43 | 6.47 ± 1.24 | 5.64 ± 1.19 |
| BHK21/HBx#22 | | 3.47 ± 0.94 | 8.95 ± 2.39 | 10.53 ± 2.94 | 10.29 ± 3.23 | 9.47 ± 3.27 |
| BHK21/HBx#42 | | 4.62 ± 1.25 | 9.74 ± 2.76 | 8.42 ± 2.54 | 8.25 ± 1.88 | 7.42 ± 1.63 |

Thus, transient co-expression of XBP1s with target genes into BHK21/HBx stable cell lines enhances the protein production compared with parental cells and the cells transfected with either HBx or XBP1s alone. Moreover, the co-transfection with HBx and XBP1s has a synergistic effect on protein production.

All the references disclosed herein are hereby incorporated herein to the extent relevant to describing, making or using the invention as claimed.

What is claimed is:

1. A method of producing a heterologous protein in mammalian host cells in culture, comprising growing mammalian host cells selected from the group consisting of HKB11 cells, CHO cells, BHK21 cells, C2C12 cells, and HEK293 cells, wherein said mammalian host cells comprise a nucleic acid encoding HBx, a nucleic acid encoding the heterologous protein, and a nucleic acid providing exogenous XBP1s, wherein the nucleic acid providing exogenous XBP1s encodes XBP1 or XBP1s, under conditions such that HBx, exogenous XBP1s and the heterologous protein are expressed by the mammalian host cells.

2. A method of producing a heterologous protein in mammalian host cells in culture, comprising growing mammalian host cells in non-adherent suspension culture, wherein said mammalian host cells comprise a nucleic acid encoding HBx, a nucleic acid encoding the heterologous protein, and a nucleic acid providing exogenous XBP1s, wherein the nucleic acid providing exogenous XBP1s encodes XBP1 or XBP1s, under conditions such that HBx, exogenous XBP1s and the heterologous protein are expressed by the mammalian host cells.

3. A method for producing a heterologous protein in mammalian host cells in culture, comprising; a) providing mammalian host cells comprising nucleic acid encoding HBx, a nucleic acid providing exogenous XBP1s, wherein the nucleic acid providing exogenous XBP1s encodes XBP1 or XBP1s, and a nucleic acid encoding the heterologous protein; and b) growing said mammalian cells under conditions such that HBx, exogenous XBP1s, and the heterologous protein are expressed by the mammalian cells.

4. The method of any one of claims 1 to 3, wherein the nucleic acid encoding HBx and/or the nucleic acid providing XBP1s is transfected into the mammalian host cells and is transiently expressed.

5. The method of any one of claims 1 to 3, wherein the culture comprises a culture medium, and the heterologous protein is secreted into the culture medium.

6. The method claim 5, further comprising recovering and/or further purifying the heterologous protein.

7. The method of one of claims 1 to 3, wherein the nucleic acid encoding HBx is stably expressed by the mammalian host cells.

8. The method of any one of claims 1 to 3, wherein the nucleic acid encoding the heterologous protein is stably expressed by the mammalian host cells.

9. The method of any one of claims 1 to 3, wherein the nucleic acid encoding the heterologous protein is transiently expressed by the mammalian host cells.

10. The method of claim 3, wherein the nucleic acid providing exogenous XBP1s is stably expressed by the mammalian host cells.

11. The method of one of claim 2 or 3, wherein said mammalian host cells are of non-hepatocyte origin.

12. The method of claim 2, wherein said mammalian host cells are DG44sus cells.

13. The method of claim 2, wherein said mammalian host cells are HEK293 cells.

* * * * *

SEQUENCE LISTING

<160> NUMBER OF SEQ ID NOS: 10

<210> SEQ ID NO 1
<211> LENGTH: 31
<212> TYPE: DNA
<213> ORGANISM: Artificial
<220> FEATURE:
<223> OTHER INFORMATION: Forward primer GER270

<400> SEQUENCE: 1
gatcacgcgt gccaccatgg ctgctaggct g             31

<210> SEQ ID NO 2
<211> LENGTH: 34
<212> TYPE: DNA
<213> ORGANISM: Artificial
<220> FEATURE:
<223> OTHER INFORMATION: Reverse primer GER271

<400> SEQUENCE: 2
gtcgactcta gattaggcag aggtgaaaaa gttg          34

<210> SEQ ID NO 3
<211> LENGTH: 31
<212> TYPE: DNA
<213> ORGANISM: Artificial
<220> FEATURE:
<223> OTHER INFORMATION: Forward primer GER275

<400> SEQUENCE: 3
gatcacgcgt gccaccatga accttgtaat g             31

<210> SEQ ID NO 4
<211> LENGTH: 31
<212> TYPE: DNA
<213> ORGANISM: Artificial
<220> FEATURE:
<223> OTHER INFORMATION: Reverse Primer GER276

<400> SEQUENCE: 4
gtcgactcta gatcaccact ggtccgaaaa c             31

<210> SEQ ID NO 5
<211> LENGTH: 18
<212> TYPE: DNA
<213> ORGANISM: Artificial
<220> FEATURE:
<223> OTHER INFORMATION: Forward primer GER212

<400> SEQUENCE: 5
tcagcagcac cctgaccc                            18

<210> SEQ ID NO 6
<211> LENGTH: 18
<212> TYPE: DNA
<213> ORGANISM: Artificial
<220> FEATURE:
<223> OTHER INFORMATION: Reverse primer GER213

<400> SEQUENCE: 6
tcagggtcag ggtgctgc                            18

<210> SEQ ID NO 7
<211> LENGTH: 20
<212> TYPE: DNA
<213> ORGANISM: Artificial

```
<220> FEATURE:
<223> OTHER INFORMATION: Forward Primer GER204

<400> SEQUENCE: 7
ggagacccaa gctggctagc                                              20

<210> SEQ ID NO 8
<211> LENGTH: 86
<212> TYPE: DNA
<213> ORGANISM: Artificial
<220> FEATURE:
<223> OTHER INFORMATION: Primer GER205

<400> SEQUENCE: 8
acgtcgccgg ccagcttcag caggtcgaag ttcagggtct gcttcacggg ggctctcttg  60
gcccgtttac ccggagacag ggagag                                       86

<210> SEQ ID NO 9
<211> LENGTH: 58
<212> TYPE: DNA
<213> ORGANISM: Artificial
<220> FEATURE:
<223> OTHER INFORMATION: Primer GER206

<400> SEQUENCE: 9
gaagctggcc ggcgacgtgg agtccaaccc cggccccatg gtgttgcaga cccaggtc    58

<210> SEQ ID NO 10
<211> LENGTH: 37
<212> TYPE: DNA
<213> ORGANISM: Artificial
<220> FEATURE:
<223> OTHER INFORMATION: Primer GER207

<400> SEQUENCE: 10
atcagtgcgg ccgcctaaca ctctcccctg ttgaagc                           37
```